US007354706B2

(12) United States Patent
Rowlen et al.

(10) Patent No.: US 7,354,706 B2
(45) Date of Patent: Apr. 8, 2008

(54) USE OF PHOTOPOLYMERIZATION FOR AMPLIFICATION AND DETECTION OF A MOLECULAR RECOGNITION EVENT

(75) Inventors: Kathy L. Rowlen, Longmont, CO (US); John W. Birks, Longmont, CO (US); Christopher Bowman, Boulder, CO (US); Hadley Sikes, Westminster, CO (US); Ryan Hansen, Boulder, CO (US); Robert Kuchta, Boulder, CO (US)

(73) Assignee: The Regents of The University of Colorado, a body corporate, Boulder, CO (US)

( * ) Notice: Subject to any disclaimer, the term of this patent is extended or adjusted under 35 U.S.C. 154(b) by 130 days.

(21) Appl. No.: 11/372,485

(22) Filed: Mar. 9, 2006

(65) Prior Publication Data

US 2006/0286570 A1 Dec. 21, 2006

Related U.S. Application Data

(63) Continuation-in-part of application No. PCT/US2004/029733, filed on Sep. 9, 2004.

(60) Provisional application No. 60/662,313, filed on Mar. 16, 2005, provisional application No. 60/501,755, filed on Sep. 9, 2003.

(51) Int. Cl.

| | |
|---|---|
| ***C12Q 1/68*** | (2006.01) |
| ***C12Q 1/70*** | (2006.01) |
| ***G01N 33/53*** | (2006.01) |

(52) U.S. Cl. .................... 435/5; 424/206.1; 424/209.1; 435/6; 435/7.1; 536/23.1

(58) Field of Classification Search .................... None
See application file for complete search history.

(56) References Cited

U.S. PATENT DOCUMENTS 4,749,647 A 6/1988 Thomas et al.

(Continued)

FOREIGN PATENT DOCUMENTS

WO WO00/43539 7/2000

(Continued)

OTHER PUBLICATIONS

Anthony et al. (2000) "Rapid Diagnosis of Bacteremia by Universal Amplification of 23S Ribosomal DNA Followed by Hybridization to an Oligonucleotide Array," *J. Clin. Microbiol.* 38:781-788.

(Continued)

*Primary Examiner*—Mary E. Mosher
*Assistant Examiner*—Stuart W. Snyder
(74) *Attorney, Agent, or Firm*—Greenlee, Winner and Sullivan, P.C.

(57) ABSTRACT

The invention provides methods to detect molecular recognition events. The invention also provides methods to detect the presence of or identify a target species based on its interaction with one or more probe species. The methods of the invention are based on amplification of the signal due to each molecular recognition event. The amplification is achieved through photopolymerization, with the polymer formed being associated with the molecular recognition event. In an embodiment, a fluorescent polymer, a magnetic polymer, a radioactive polymer or an electrically conducting polymer can form the basis of detection and amplification. In another embodiment, a polymer gel swollen with a fluorescent solution, a magnetic solution, a radioactive solution or an electrically conducting solution can form the basis of detection and amplification. In another embodiment, sufficient polymer forms to be detectable by visual inspection.

26 Claims, 6 Drawing Sheets

10 2 12 50 I 20 40 22 30 20 22 35 20 25 M, light 60 37 20 27

U.S. PATENT DOCUMENTS

| | | | |
|---|---|---|---|
| 4,876,187 A | 10/1989 | Duck et al. | |
| 5,011,769 A | 4/1991 | Duck et al. | |
| 5,019,496 A | 5/1991 | Oster et al. | |
| 5,124,246 A | 6/1992 | Urdea et al. | |
| 5,175,270 A | 12/1992 | Nilsen et al. | |
| 5,185,243 A | 2/1993 | Ullman et al. | |
| 5,196,306 A | 3/1993 | Bobrow et al. | |
| 5,359,100 A | 10/1994 | Urdea et al. | |
| 5,403,711 A | 4/1995 | Walder et al. | |
| 5,449,602 A * | 9/1995 | Royer et al. | 435/6 |
| 5,484,904 A | 1/1996 | Nilsen et al. | |
| 5,487,973 A | 1/1996 | Nilsen et al. | |
| 5,545,730 A | 8/1996 | Urdea et al. | |
| 5,571,670 A | 11/1996 | Urdea et al. | |
| 5,573,907 A | 11/1996 | Carrino et al. | |
| 5,580,731 A | 12/1996 | Chang et al. | |
| 5,591,584 A | 1/1997 | Chang et al. | |
| 5,594,117 A | 1/1997 | Urdea et al. | |
| 5,594,118 A | 1/1997 | Urdea et al. | |
| 5,597,909 A | 1/1997 | Urdea et al. | |
| 5,624,802 A | 4/1997 | Urdea et al. | |
| 5,635,352 A | 6/1997 | Urdea et al. | |
| 5,637,460 A | 6/1997 | Swan et al. | |
| 5,660,988 A | 8/1997 | Duck et al. | |
| 5,681,697 A | 10/1997 | Urdea et al. | |
| 5,681,702 A | 10/1997 | Collins et al. | |
| 5,710,264 A | 1/1998 | Urdea et al. | |
| 5,770,722 A | 6/1998 | Lockhart et al. | |
| 6,096,369 A | 8/2000 | Anders et al. | |
| 6,361,944 B1 | 3/2002 | Mirkin et al. | |
| 6,372,937 B1 | 4/2002 | Bobrow et al. | |
| 6,406,845 B1 | 6/2002 | Walt et al. | |
| 6,417,340 B1 | 7/2002 | Mirkin et al. | |
| 6,485,703 B1 | 11/2002 | Cote et al. | |
| 6,495,324 B1 | 12/2002 | Mirkin et al. | |
| 6,506,564 B1 | 1/2003 | Mirkin et al. | |
| 6,582,921 B2 | 6/2003 | Mirkin et al. | |
| 6,593,100 B2 | 7/2003 | Bobrow et al. | |
| 6,602,669 B2 | 8/2003 | Letsinger et al. | |
| 6,610,491 B2 | 8/2003 | Mirkin et al. | |
| 6,645,721 B2 | 11/2003 | Mirkin et al. | |
| 6,667,122 B2 | 12/2003 | Kayfmann | |
| 6,673,548 B2 | 1/2004 | Mirkin et al. | |
| 6,682,895 B2 | 1/2004 | Mirkin et al. | |
| 6,709,825 B2 | 3/2004 | Mirkin et al. | |
| 6,720,147 B2 | 4/2004 | Mirkin et al. | |
| 6,720,411 B2 | 4/2004 | Mirkin et al. | |
| 6,730,269 B2 | 5/2004 | Mirkin et al. | |
| 6,740,491 B2 | 5/2004 | Mirkin et al. | |
| 6,750,016 B2 | 6/2004 | Mirkin et al. | |
| 6,759,199 B2 | 7/2004 | Mirkin et al. | |
| 6,767,702 B2 | 7/2004 | Mirkin et al. | |
| 6,773,884 B2 | 8/2004 | Mirkin et al. | |
| 6,777,186 B2 | 8/2004 | Mirkin et al. | |
| 6,806,047 B2 | 10/2004 | Goldberg et al. | |
| 2002/0071943 A1 | 6/2002 | Hawker et al. | |
| 2003/0236425 A1 | 12/2003 | Herr et al. | |
| 2004/0063146 A1 | 4/2004 | Sayre et al. | |

FOREIGN PATENT DOCUMENTS

WO WO2004/093845 11/2004

OTHER PUBLICATIONS

Baner et al. (1998) "Signal Amplification of Padlock Probes by Rolling Circle Replication," *Nuc. Acids Res* 26:5073-5078.

Barany, F. (1991) "Genetic Disease Detection and DNA Amplification Using Cloned Thermostable Ligase," *Proc. Natl. Acad. Sci. USA* 88:189-193.

Biesalski et al. (1999) "Segment Density Profiles of Polyelectrolyte Brushes Determined by Fourier Transform Ellipsometry," *J. Chem. Phys.* 111(15):7029-7037.

Bontempo et al. (Apr. 2005) "Streptavidin as a Macroinitiator for Polymerization: In Situ Protein-Polymer Conjugate Formation", J. Am. Chem. Soc. 127(18), 6508-6509.

Constans (Aug. 2004) "Protein Microarrays Mature," *The Scientist* 18(15):42.

Daubendiek et al. (1997) "Generation of Catalytic RNA's by Rolling Transcription of Synthetic DNA Nanocircles," *Nat. Biotech.* 15:273-277.

Husemann et al. (1999) "Surface Initiated Polymerization for Amplification of Self-Assembled Monolayers Patterned by Microcontact Printing," *Angew. Chem. Int. Ed.* 38(5):647-649.

International Search Report Corresponding to International Application No. PCT/US04/029733, Mailed Mar. 24, 2005.

International Search Report Corresponding to International Application No. PCT/US05/08807, Mailed May 2, 2006.

Kern et al. (1996) "An Enhanced-Sensitivity Branched-DNA Assay for Quantification of Human Immunodeficiency Virus Type 1 RNA in Plasma," *J. Clin. Microbiol.* 34:3196-3203.

Li et al. (2001) "Typing and Subtyping Influenza Virus Using DNA Microarrays and Multiplex Reverse Transcriptionase PCR," *J. Clin. Microbiol.* 39(2):696-704.

Lizardi et al. (1998) "Mutation Detection and Single-Molecule Counting Using Isothermal Rolling-Circle Amplification," *Nat. Genet.* 19:225-232.

Lou et al. (Jul. 2005) "Detection of DNA Point Mutation by Atom Transfer Radical Polymerization", *Anal. Chem.* 77, 4698-4705.

Nallur et al. (2001) "Signal Amplification by Rolling Circle Amplification on DNA Microarrays," *Nuc. Acids Res.* 29:E118.

Park et al. (Feb. 2002) "Array-Based Electrical Detection of DNA with Nanoparticle Probes," *Science* 295:1503-1506.

Risberg, E. (Apr. 2003) "Gene Chip Helps Identify Cause of Mystery Illness," *USA Today* Jun. 15, 2003.

Schena, M. (2003) *Microarray Analysis*, John Wiley and Sons, New Jersey, pp. 8,117,151,153,154.

Shah et al. (2000) "Using Atom Transfer Radical Polymerization to Amplify Monolayers of Initiators Patterned by Microcontact Printing into Polymer Brushed for Pattern Transfer," *Macromol.* 33:597-605.

Sikes et al. (Oct. 2007) "Using polymeric materials to generate an amplified response to molecular recognition events", *Nature Materials* doi:10.1038/n mat2042.

Stears et al. (2000) "A Novel, Sensitive Detection System for High-Density Microarrays Using Dendrimer Technology," *Physiol. Genomics* 3:93-99.

Vernet, G. (2001) "DNA-Chip Technology and Infectious Diseases," *Virus Res.* 82:65-71.

Wang et al (Sep. 2002) "Microarray Based Detection and Genotyping of Viral Pathogens," *Proc. Nat. Acad. Sci. USA* 99(24):15687-15692.

Xu et al. (2001) "Microfabricated Disposable DNA Sensors Based on Enzymatic Amplification Electrochemical Detection," *Electroanalysis* 13(10):882-887.

Zhang et al. (1998) "Amplification of Target-Specific, Ligation-Dependent Circular Probe," *Gene* 211:277-285.

Hansen et al. (Dec. 1, 2007) "Visual Detection of Labeled Oligonucleotides Using Visible Light-Polymerization-Based Amplification," *Biomacromolecules* , DOI 10.1021/bm700672z.

Lou et al. (Jan. 2006) "DNA-Accelerated Atom Transfer Radical Polymerization on a Gold Surface," Langmuir, 22, 2640-2646.

* cited by examiner

USE OF PHOTOPOLYMERIZATION FOR AMPLIFICATION AND DETECTION OF A MOLECULAR RECOGNITION EVENT

CROSS-REFERENCE TO RELATED APPLICATIONS

This application is a continuation-in-part of International Application Ser. No. PCT/US2004/029733, filed Sep. 9, 2004, and claims the benefit of U.S. provisional application Ser. No. 60/662,313, filed Mar. 16, 2005; International Application PCT/US2004/029733 claims the benefit of U.S. provisional application Ser. No. 60/501,755, filed on Sep. 9, 2003, all of which are hereby incorporated by reference to the extent not inconsistent with the disclosure herein.

ACKNOWLEDGEMENT OF GOVERNMENT SUPPORT

This invention was made at least in part with support from the National Institutes of Health under grant number NIH HG003100 and the US Air Force under grant number AFOSR F49620-02-1-0042. The United States Government has certain rights in this invention.

BACKGROUND OF THE INVENTION

This invention is in the field of detection of molecular recognition events, in particular use of photopolymerization for amplification and detection of these events.

A variety of methods exist for detection of molecular recognition events. Detection of molecular recognition events such as DNA hybridization, antibody-antigen interactions, and protein-protein interactions becomes increasingly difficult as the number of recognition events to be detected decreases. Of particular interest are molecular recognition events between a target and a probe.

One approach to the problem is to increase the number of recognition events taking place. For example, polymerase chain reaction (PCR) increases the number of copies of DNA or RNA to be detected. Other molecular biology techniques which increase the number of copies of DNA or RNA to be detected include reverse transcription polymerase chain reaction (RT-PCR), strand displacement amplification, and Eberwine linear amplification.

Another approach is to amplify the signal due to each molecular recognition event. For example, DNA detection methods based on oligonucleotide-modified particles have been reported (U.S. Pat. Nos. 6,740,491, 6,777,186, 6,773,884, 6,767,702, 6,759,199, 6,750,016, 6,730,269, 6,720,411, 6,720,147, 6,709,825, 6,682,895, 6,673,548, 6,667,122, 6,645,721, 6,610,491, 6,582,921, 6,506,564, 6,495,324, 6,417,340 and 6,361,944 and Park, S.-J. et al, 2002, Science, 295,5559, 1503-1506). U.S. Pat. No. 6,602,669 relates to silver staining nanoparticles.

DNA detection methods based on branched DNA have also been reported (U.S. Pat. Nos. 5,681,702, 5,597,909, 5,580,731, 5,359,100, 5,124,246, 5,545,730, 5,594,117, 5,571,670, 5,594,118, 5,681,697, 5,591,584, 5,571,670, 5,624,802, 5,635,352, and 5,591,584. The branched DNA assay is a solution phase assay that involves a number of probe oligonucleotides that bind to multiple sites on the target viral RNA. Detection is possible because each hybridization event is accompanied by the binding of a fluorophore (Kern, D., Collins, M., Fultz, T., Detmer, J., Hamren, S., Peterkin, J., Sheridan, P., Urdea, M., White, R., Yeghiazarian, T., Todd, J. (1996) "An Enhanced-sensitivity Branched-DNA Assay for Quantification of Human Immunodeficiency Virus Type 1 RNA in Plasma" Journal of Clinical Microbiology 34:3196-3203). The synthetic effort required for this assay is relatively large: multiple probes are designed for each RNA of interest, and the assay depends on the binding of these probes to multiple preamplifier and amplifier molecules that also must be designed and synthesized.

Dendrimer-based DNA detection methods have also been reported (U.S. Pat. Nos. 5,710,264, 5,175,270, 5,487,973, 5,484,904 and Stears, R. et al., 2000, Physiol. Genomics 3: 93-99). Dendrimers are complexes of partially double-stranded oligonucleotides, which form stable, spherical structures with a determined number of free ends. Specificity of the dendrimer detection is accomplished through specific binding of a capture oligonucleotide on a free arm of the dendrimer. Other arms of the dendrimer are labeled for detection. This method does not require enzymes and can produce amplification of 300-400.

Tyramide signal amplification is reported in U.S. Pat. Nos. 6,593,100 and 6,372,937.

Rolling circle amplification has been described in the scientific literature (Baner et al. (1998) Nuc. Acids Res. 26:5073-5078; Barany, F. (1991) Proc. Natl. Acad. Sci. USA 88:189-193; Lizardi et al. (1998), Nat. Genet. 19:225-232; Zhang et al., Gene 211:277 (1998); and Daubendiek et al., Nature Biotech. 15:273 (1997)). Rolling circle amplification is capable of detecting as few as 150 molecules bound to a microarray (Nallur, G., Luo, C., Fang, L., Cooley, S., Dave, V., Lambert, J., Kukanskis, K., Kingsmore, S., Lasken, R., Schweitzer, B. (2001) "Signal Amplification by Rolling Circle Amplification on DNA Microarrays" *Nucleic Acids Research* 29:E1 18). The main drawback to RCA is the necessity of DNA polymerase.

Ligase chain reaction is reported in U.S. Pat. Nos. 5,185,243 and 5,573,907.

Cycling probe technology is reported in U.S. Pat. Nos. 5,011,769, 5,403,711, 5,660,988, and 4,876,187.

Microfabricated disposable DNA sensors based on enzymatic amplification electrochemical detection was reported by Xu et al. (Xu et al., 2001, Electoanalysis, 13(10), 882-887).

Surface initiated polymerization from surface confined initiators has been reported. Biesalski et al. report poly (methyl methacrylate) brushes grown in situ by free radical polymerization from an azo-initiator monolayer covalently bound to the surface (Biesalski, M. et al., (1999), J. Chem. Phys., 111 (15), 7029). Surface initiated polymerization for amplification of patterned self-assembled monolayers by surface-initiated ring opening polymerization (Husemann, M. et al., Agnewandte Chemie Int. Ed. (1999), 38(5) 647-649) and atom transfer radical polymerization (Shah, R. R. et al., (2000), Macromolecules, 33, 597-605) has been also reported.

DNA microarrays, or biochips, represent promising technology for accurate and relatively rapid pathogen identification (Wang, D., Coscoy, L., Zylberberg, M., Avila, P. C., Boushey, H. A., Ganem, D., DeRisi, J. L. (2002) "Microarray Based Detection and Genotyping of Viral Pathogens," *PNAS*, 99(24), 15687-15692). Anthony et al. recently demonstrated rapid identification of 10 different bacteria in blood cultures using a BioChip (Anthony, R. M., Brown, T. J., French, G. L. (2000) "Rapid Diagnosis of Bacteremia by Universal Amplification of 23S Ribosomal DNA Followed by Hybridization to an Oligonucleotide Array" *Journal of Clinical Microbiology* 38:781-788). The microarray assay was conducted in ~4 hrs. The approach utilized universal primers for PCR amplification of the variable region of bacterial 23s ribosomal DNA, and a 3×10 array of 30 unique capture sequences. This work demonstrates an important aspect of BioChip platforms—the capability to screen for multiple pathogens simultaneously. DeRisi and co-workers demonstrated a "virus chip" that contained sequences for hundreds of viruses, including many that cause respiratory illness (Wang et al., 2002). This chip proved useful in identifying the corona virus associated with SARS (Risberg, E. (2003) "Gene Chip Helps Identify Cause of Mystery Illness," USA Today (Jun. 18, 2003)). Evans and co-workers have demonstrated that a DNA microarray could be used for typing and sub-typing human influenza A and B viruses (Li, J., Chen, S., & Evans, D. H. (2001) "Typing and Subtyping Influenza Virus Using DNA Microarrays and Multiplex Reverse Transcriptase PCR" *Journal of Clinical Microbiology* 39:696-704). In both the DeRisi and Evans work PCR technology was used to amplify the genetic material for capture and relatively expensive fluorescent labels (~$50 in labels per chip) were used to generate signals from positive spots.

There remains a need in the art for relatively inexpensive labeling and signal amplification methods for molecular recognition events which do not require the use of enzymes for amplification. These methods would be useful in combination with DNA microarrays.

SUMMARY OF THE INVENTION

In an embodiment, the invention provides methods to detect molecular recognition events, in particular a relatively small number of molecular recognition events. The methods of the invention are based on amplification of the signal due to each molecular recognition event, rather than amplification of the number of molecular recognition events taking place. The present invention can limit or eliminate the need for techniques which increase the number of recognition events taking place, including PCR and techniques involving culturing of bacteria. The present invention can replace PCR and RT-PCR techniques for microarray applications as a means to achieve acceptable signals.

In general, the methods of the invention can be used to generate and amplify a signal due to many types of molecular recognition events that can be described by the following equation:

$$A+B+In \rightarrow A-B-In \quad \text{(Eqn. 1)}$$

where A and B are the species of interest that undergo molecular recognition and In is a photoinitiator. A is the probe species and B is the target species. For a microarray, the probe A is attached to the substrate. The target species, B, and/or the photoinitiator may comprise a linking group which allows selective binding of the photoinitiator to the target or the A-B complex. As an example, the target species may comprise biotin and the initiator avidin.

When the initiator comprises a linking group, Equation 1 may also be written as:

$$A+B+C-In \rightarrow A-B-C-In \quad \text{(Eqn. 2)}$$

where C comprises an entity which allows selective binding of the photoinitiator to the target or the A-B complex.

The amplification scheme relies on the large number of propagation events that occur for each initiation event. Depending on the specific polymerization system used (light intensity, initiator concentration, monomer formulation, temperature, etc.), each initiator can lead to the polymerization of as many as $10^2$-$10^6$ monomer units. Thus, each single molecular recognition event has the opportunity to be amplified by the polymerization of up to $10^6$ monomers, each of which may be fluorescent or enable detection of its presence through one of a variety of means. In an embodiment, a fluorescent polymer, a magnetic polymer, a radioactive polymer or an electrically conducting polymer can form the basis of detection and amplification. In another embodiment, a polymer gel swollen with a fluorescent solution, a magnetic solution, a radioactive solution or an electrically conducting solution can form the basis of detection and amplification.

In another embodiment, the quantity of polymer formed is sufficient to allow visual detection of polymer formation. In this embodiment, the polymer need not be fluorescent, magnetic, radioactive or electrically conducting. This embodiment can be achieved through a synergistic combination of reduction of oxygen content in the polymer precursor solution by purging, utilization of a macroinitiator with an appropriate ratio of initiator to molecular recognition agent, and the identification of the appropriate exposure time. Without wishing to be bound by any particular belief, it is believed that a process having all these attributes can yield much higher degrees of amplification and enable better contrast than is possible with a process having only one of these attributes.

In an embodiment, the invention provides a method for amplifying a molecular recognition interaction between a target and a probe comprising the steps of:

a. contacting the target with the probe under conditions effective to form a target-probe complex;
b. removing target not complexed with the probe;
c. contacting the target-probe complex with a photoinitiator label under conditions effective to attach the photoinitiator label to the target-probe complex;
d. removing photoinitiator label not attached to the target-probe complex;
e. contacting the photoinitiator-labeled target-probe complex with a polymer precursor solution;
f. exposing the photoinitiator-labeled target-probe complex and the polymer precursor solution to light, thereby forming a polymer; and
g. detecting the polymer formed, thereby detecting an amplified target-probe interaction.

In an embodiment, the invention provides a method for amplifying a molecular recognition interaction between a target and a probe comprising the steps of:

a. contacting the target with the probe under conditions effective to form a target-probe complex;
b. removing target not complexed with the probe;
c. contacting the target-probe complex with a photoinitiator label under conditions effective to attach the photoinitiator label to the target-probe complex;
d. removing photoinitiator label not attached to the target-probe complex;
e. contacting the photoinitiator-labeled target-probe complex with a polymer precursor solution;
f. exposing the photoinitiator-labeled target-probe complex and the polymer precursor solution to light, thereby forming a polymer; and
g. detecting the polymer formed, thereby detecting an amplified target-probe interaction, wherein the photoinitiator label is a macroinitiator and the oxygen content of the polymer precursor solution during light exposure is sufficiently low and the time of light exposure is sufficiently long that the polymer forms in sufficient quantities to allow visual detection.

In another embodiment, the invention provides methods for identification of a target species based on its molecular interaction with an array of different probe species, each probe species being attached to a solid substrate at known locations. In the methods of the invention, if the target species undergoes a molecular recognition reaction with a probe, the probe will be labeled with a polymer. Detection of the polymer-labeled probes allows identification of which probes have undergone the molecular recognition reaction and therefore identification of the target.

In an embodiment, the invention provides a method for identifying a target comprising the steps of:

a. providing a probe array comprising a plurality of different probes, wherein the probes are attached to a solid substrate at known locations;
b. contacting the probe array with the target under conditions effective to form a target-probe complex;
c. removing target not complexed with the probe;
d. contacting the target-probe complex with a photoinitiator label under conditions effective to attach the label to the target-probe complex;
e. removing photoinitiator label not attached to the target-probe complex;
f. contacting the photoinitiator-labeled target-probe complex with a polymer precursor solution;
g. exposing the photoinitiator-labeled target-probe complex and the polymer precursor to light, thereby forming a polymer; and
h. detecting the polymer formed, wherein the polymer location indicates the probe which forms a target-probe complex with the target, thereby identifying the target.

In an embodiment, the invention provides a method for identifying a target comprising the steps of:

a. providing a probe array comprising a plurality of different probes, wherein the probes are attached to a solid substrate at known locations;
b. contacting the probe array with the target under conditions effective to form a target-probe complex;
c. removing target not complexed with the probe;
d. contacting the target-probe complex with a photoinitiator label under conditions effective to attach the label to the target-probe complex;
e. removing photoinitiator label not attached to the target-probe complex;
f. contacting the photoinitiator-labeled target-probe complex with a polymer precursor solution;
g. exposing the photoinitiator-labeled target-probe complex and the polymer precursor solution to light, thereby forming a polymer; and
h. detecting the polymer formed, wherein the polymer location indicates the probe which forms a target-probe complex with the target, thereby identifying the target, wherein the photoinitiator label is a macroinitiator and the oxygen content of the polymer precursor solution during light exposure is sufficiently low and the time of light exposure is sufficiently long that the polymer forms in sufficient quantities to allow visual detection.

The methods of the invention can be used to identify target species using DNA microarrays, also commonly referred to as DNA chips or BioChips, to provide the probe array. In an embodiment, the DNA microarray may be an array which allows identification and strain analysis for one or more genera of influenza virus.

In an embodiment, the methods of the invention provide sufficient amplification that molecular recognition can be detected without instrumentation. In another embodiment, the methods of the invention provide sufficient amplification that molecular recognition can be detected using a relatively inexpensive microarray reader or scanner which may not have the highest instrument sensitivity or resolution.

BRIEF SUMMARY OF THE FIGURES

FIG. 3A is an image of the array after polymerization;

FIG. 3B shows negative control spots on the same array.

DETAILED DESCRIPTION OF THE INVENTION

Figure 1:
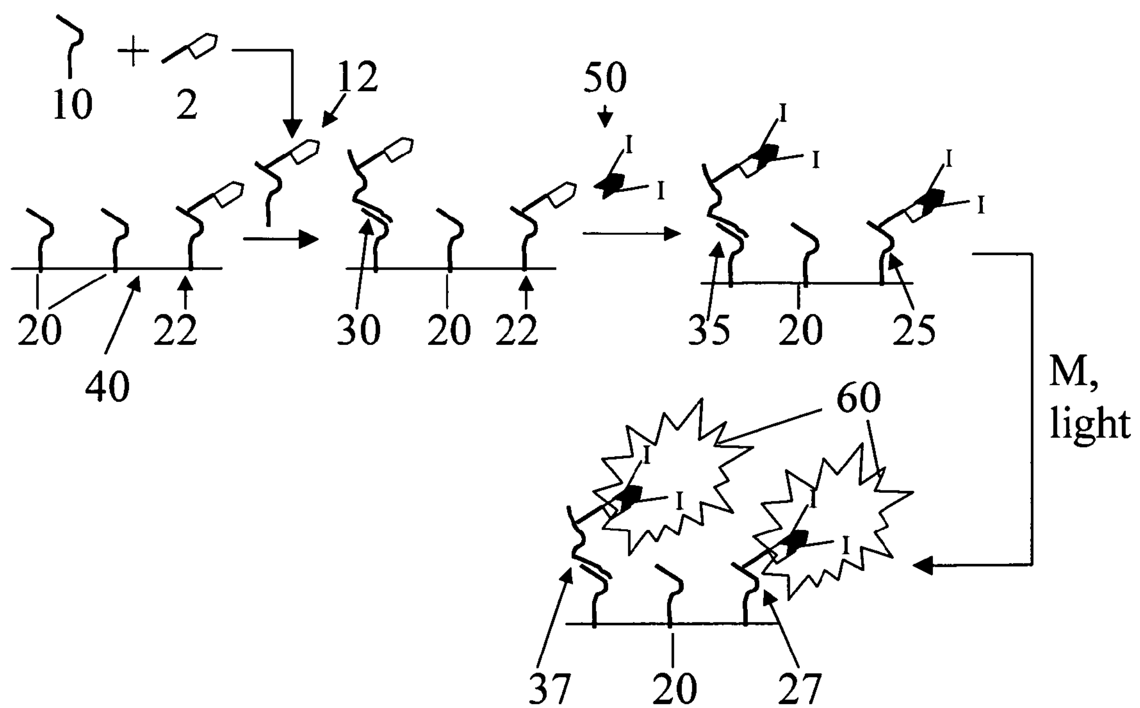
FIG. 1 schematically illustrates some of the steps in detection and amplification of hybridization using photopolymerization.

FIG. 1 is a conceptual diagram of how photopolymerization of a fluorescent monomer M is used to generate and amplify a signal from a single captured genetic target on a DNA microarray. FIG. 1 shows addition of biotin (2) to the target oligonucleotide (10) to form a biotinylated target nucleotide (12). The biotinylated target nucleotide (12) is hybridized to a complementary probe (20), forming a target-probe complex (30) on the surface of the microarray (40). The microarray shown in FIG. 1 contains a biotin-labeled probe (22) which acts as a positive control. After hybridization, the microarray is exposed to a photoinitiator label (50), initiator-functionalized avidin, which interacts with the biotinylated target oligonucleotide (12) and control probe (22) to form an initiator-labeled target-probe complex (35) and an initiator-labeled positive control probe (25). The microarray surface is then exposed to a fluorescent monomer (M) under the appropriate initiation conditions. In the presence of light and a fluorescent monomer (represented by M in FIG. 1), a polymerization reaction occurs from sites on the surface where targets have been captured by the probe DNA, forming a polymer-labeled target-probe complex (37) and a polymer-labeled positive control probe (27). In FIG. 1, the polymer label is denoted by (60). Ideally, since initiators are not bound to sites where hybridization has not occurred, polymerization does not occur from those sites. For brevity, FIG. 1 omits several steps which are typically used in the process, including removal of uncomplexed target material prior to exposure of the microarray to initiator functionalized avidin, removal of initiator functionalized avidin not attached to the target-probe complex, and removal of unpolymerized monomer prior to detection.

Although FIG. 1 illustrates hybridization of complementary DNA to a DNA microarray as a specific example, the detection and amplification scheme generalizes to many other types of molecular recognition events. Agents capable of participating in molecular recognition events include, but are not limited to, agonists and antagonists for cell membrane receptors, toxins and venoms, viral epitopes, hormones (e.g., opiates, steroids, etc.), hormone receptors, peptides, enzymes, enzyme substrates, substrate analogs, transition state analogs, cofactors, drugs, proteins, and antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. In different embodiments, the detection and amplification scheme can be used to detect and amplify the molecular recognition interaction between nucleic acids, an antibody and an antigen, and a first and a second protein. Microarrays can be used to detect hybridization as well as protein-protein interactions, protein drug binding, and enzymatic catalysis (Schena, M., "Microarray Analysis, (2003) John Wiley & Sons, New Jersey, p. 153). As used herein, molecular recognition interactions are those in which the probe recognizes and selectively binds a target, resulting in a target-probe complex. Molecular recognition interactions also involve the formation of noncovalent bonds between the two species. The binding occurs between specific regions of atoms (molecular domains) on the probe species which have the characteristic of binding or attaching specifically to unique molecular domains on specific target species. Molecular recognition interactions can also involve responsiveness of one species to another based on the reciprocal fit of a portion of their molecular shapes.

The target and probe are two species of interest which undergo molecular recognition. The target may also be referred to as a ligand. The probe may also be referred to as a receptor. In an embodiment, at least some characteristics of the probe are known. In an embodiment, the probe is an oligonucleotide whose sequence is known or partially known. In other embodiment, the sequence of the probe may not be known, but it is known to be complementary to a possible target species. Typically, the probe will be selected so that it is capable of selected recognition with the known or suspected identity of the target. In some cases a single probe can be used to detect the presence of a target. In other cases more than one probe will be necessary to detect the presence of or identify a target.

In order for molecular interaction between the target and the probe to identify the target, the molecular interaction between the target and the probe must be sufficiently specific. For hybridization, the selectivity is a measure of the specificity of the molecular recognition event. "Selectivity" or "hybridization selectivity" is the ratio of the amount of hybridization (i.e., number of second nucleic acids hybridized) of fully complementary hybrids to partially complementary hybrids, based on the relative thermodynamic stability of the two complexes. For the purpose of this definition it is presumed that this ratio is reflected as an ensemble average of individual molecular binding events. Selectivity is typically expressed as the ratio of the amount of hybridization of fully complementary hybrids to hybrids having one base pair mismatches in sequence. Selectivity is a function of many variables, including, but not limited to,: temperature, ionic strength, pH, immobilization density, nucleic acid length, the chemical nature of the substrate surface and the presence of polyelectrolytes and/or other oligomers immobilized on the substrate or otherwise associated with the immobilised film.

For hybridization, the homology of the target and probe molecules influences whether hybridization occurs. Cross-hybridization can occur if the sequence identity between the target and the probe is greater than or equal to about 70% (Schena, M., "Microarray Analysis, (2003) John Wiley & Sons, New Jersey, p. 151).

In an embodiment, either the target or the probe is a nucleic acid. In an embodiment, both the target and the probe are a single stranded nucleic acid. In an embodiment, the probe is an oligonucleotide, a relatively short chain of single-stranded DNA or RNA. "Nucleic acid" includes DNA and RNA, whether single or double stranded. The term is also intended to include a strand that is a mixture of nucleic acids and nucleic acid analogs and/or nucleotide analogs, or that is made entirely of nucleic acid analogs and/or nucleotide analogs and that may be conjugated to a linker molecule. "Nucleic acid analogue" refers to modified nucleic acids or species unrelated to nucleic acids that are capable of providing selective binding to nucleic acids or other nucleic acid analogues. As used herein, the term "nucleotide analogues" includes nucleic acids where the internucleotide phosphodiester bond of DNA or RNA is modified to enhance bio-stability of the oligomer and "tune" the selectivity/specificity for target molecules (Uhlmann, et al., (1990), Angew. Chem. Int. Ed. Eng., 90: 543; Goodchild, (1990), J. Bioconjugate Chem., 1: 165; Englisch et al., (1991), Angew, Chem. Int. Ed. Eng., 30: 613). Such modifications may include and are not limited to phosphorothioates, phosphorodithioates, phosphotriesters, phosphoramidates or methylphosphonates. The 2'-O-methyl, allyl and 2'-deoxy-2'-fluoro RNA analogs, when incorporated into an oligomer show increased biostability and stabilization of the RNA/DNA duplex (Lesnik et al., (1993), Biochemistry, 32: 7832). As used herein, the term "nucleic acid analogues" also include alpha anomers ($\alpha$-DNA), L-DNA (mirror image DNA), 2'-5' linked RNA, branched DNA/RNA or chimeras of natural DNA or RNA and the above-modified nucleic acids. For the purposes of the present invention, any nucleic acid containing a "nucleotide analogue" shall be considered as a nucleic acid analogue. Backbone replaced nucleic acid analogues can also be adapted to for use as immobilised selective moieties of the present invention. For purposes of the present invention, the peptide nucleic acids (PNAs) (Nielsen et al., (1993), Anti-Cancer Drug Design, 8: 53; Engels et al., (1992), Angew, Chem. Int. Ed. Eng., 31: 1008) and carbamate-bridged morpholino-type oligonucleotide analogs (Burger, D. R., (1993), J. Clinical Immunoassay, 16: 224; Uhlmann, et al., (1993), Methods in Molecular Biology, 20,. "Protocols for Oligonucleotides and Analogs," ed. Sudhir Agarwal, Humana Press, NJ, U.S.A., pp. 335-389) are also embraced by the term "nucleic acid analogues". Both exhibit sequence-specific binding to DNA with the resulting duplexes being more thermally stable than the natural DNA/DNA duplex. Other backbone-replaced nucleic acids are well known to those skilled in the art and can also be used in the present invention (See e.g., Uhlmann et al., (1993), Methods in Molecular Biology, 20, "Protocols for Oligonucleotides and Analogs," ed. Sudhir Agrawal, Humana Press, NJ, U.S.A., pp. 335).

More generally, the probe and/or target can be an oligomer. "Oligomer" refers to a polymer that consists of two or more monomers that are not necessarily identical. Oligomers include, without limitation, nucleic acids (which include nucleic acid analogs as defined above), oligoelectrolytes, hydrocarbon based compounds, dendrimers, nucleic acid analogues, polypeptides, oligopeptides, polyethers, oligoethers any or all of which may be immobilized to a substrate. Oligomers can be immobilized to a substrate surface directly or via a linker molecule.

In an embodiment, the probe is DNA. The DNA may be genomic DNA or cloned DNA. The DNA may be complementary DNA (cDNA), in which case the target may be messenger RNA (mRNA). The DNA may also be an Expressed Sequence Tag (EST) or a Bacterial Artificial Chromosome (BAC). For use in hybridization microarrays, double-stranded probes are denatured prior to hybridization, effectively resulting in single-stranded probes.

DNA microarrays are known to the art and commercially available. The general structure of a DNA microarray is a well defined array of spots on an optically flat surface, each of which contains a layer of relatively short strands of DNA. As referred to herein, microarrays have a spot size less than about 1.0 mm. In most hybridization experiments, 15-25 nucleotide sequences are the minimum oligonucleotide probe length (Schena, M., "Microarray Analysis, (2003) John Wiley & Sons, New Jersey, p. 8). The substrate is generally flat glass primed with an organosilane that contains an aldehyde functional group. The aldehyde groups facilitate covalent bond formation to biomolecules with free primary amines via Schiff base interactions. After reaction the chip is cured to form a very stable array ready for hybridization.

Protein microarrays are also known to the art and some are commercially available. The general structure of protein microarrays can be similar to that of DNA microarrays, except that array spots can contain antibodies (in particular monoclonal antibodies), antigens, recombinant proteins, or peptides. For accurate measurement of binding events, surface-bound proteins must be correctly folded and fully functional (Constans, A. , 2004, The Scientist, 18(15) 42). To reduce protein unfolding, the proteins can be protected by use of stabilizing buffers and/or relatively high protein concentrations (Schena, M., "Microarray Analysis, (2003) John Wiley & Sons, New Jersey, p. 154). To avoid the protein folding problem, the functional domains of interest can be arrayed rather than the whole protein, forming domain-based arrays (Constans, 2004, ibid).

In an embodiment, the target is genetic material from influenza A, B, or C. Influenza is an orthomyxovirus with three genera, types A, B, and C. The types are distinguished by the nucleoprotein antigenicity (Dimmock, N. J., Easton, A. J., Leppard, K. N. (2001) "Introduction to Modern Virology" 5$^{th}$ edition, Blackwell Science Ltd., London). Influenza A and B each contain 8 segments of negative sense ssRNA. Type A viruses can also be divided into antigenic sub-types on the basis of two viral surface glycoproteins, hemagglutinin (HA) and neuraminidase (NA). There are currently 15 identified HA sub-types (designated H1 through H15) and 9 NA sub-types (N1 through N9) all of which can be found in wild aquatic birds (Lamb, R. A. & Krug, R. M., (1996) "Orthomyxoviridae: The Viruses and their Replication, in Fields Virology", B. N. Fields, D. M. Knipe, and P. M. Howley, Editors. Lippincott-Raven: Hagerstown). Of the 135 possible combinations of HA and NA, only four (H1N1, H1N2, H2N2, and H3N2) have widely circulated in the human population since the virus was first isolated in 1933. The two most common sub-types of influenza A currently circulating in the human population are H3N2 and H1N1. L1 et al. describe a DNA microarray whose probes were multiple fragments of the hemagglutinin, neuraminidase, and matrix protein genes. (Li, J. et al., (2001), J. Clinical Microbio., 39(2), 696-704).

For probes bound to a substrate using aldehyde attachment chemistry, the substrate may be treated with an agent to reduce the remaining aldehydes prior to contacting the probe with the target. One suitable reducing agent is sodium borohydride $NaBH_4$. Such a treatment can decrease the amount of reaction between the monomer and the aldehyde coating on the glass, thus decreasing the amount of background signal during the detection step.

Prior to contacting the target with the probe, the target may be biotinylated to allow later attachment of at least one initiator via biotin-avidin interaction. In an embodiment, photobiotinylation reagents (Pierce, Quanta Biodesign) can be used to biotin-label the target.

In an embodiment, the target may be contacted with the photoinitiator label prior to contacting the target with the probe, so long as use of a photoinitiator-labeled target does not substantially limit its participation in the desired molecular recognition event. In an embodiment, the invention provides a method for amplifying a molecular recognition interaction between a target and a probe comprising the steps of contacting a photoinitiator-labeled target with a probe under conditions effective to form a photoinitiator-labeled target-probe complex, removing target not complexed with the probe, contacting the photoinitiator-labeled target-probe complex with a polymer precursor, exposing the photoinitiator-labeled target-probe complex and the polymer precursor to light, thereby forming a polymer, and detecting the polymer formed, thereby detecting an amplified target-probe interaction.

The probe is contacted with a solution comprising the target under conditions effective to form a target-probe complex. The conditions effective to form a target-probe complex depend on the target and probe species. For ssDNA or RNA targets binding to ssDNA probes, suitable hybridization conditions have been described in the scientific literature. In an embodiment, it is sufficient to contact a solution comprising the target with the probe for about 2 hours at about 42° C. In an embodiment, this solution also comprises an agent, such as a crowding agent, to limit nonspecific interactions. With reference to nucleic acid interactions, a crowding agent is an agent that interrupts nonspecific adsorption between nucleic acids that are not complementary. Formamide is one such agent to limit nonspecific interactions (Stahl, D. A., and R. Amann. 1991. Development and application of nucleic acid probes, p.205-248. In E. Stackebrandt and M. Goodfellow (ed.), Nucleic acid techniques in bacterial systematics. John Wiley & Sons Ltd., Chichester, United Kingdom). Nonspecific interactions can also be limited by applying a blocking agent to the microarray prior to contacting the target with the probe. Suitable blocking agents are known to the art and include, but are not limited to barine serum albumin (BSA), nonfat milk, and sodium borohydride. Detergents such as sodium lauroyl sarcosine or sodium dodecyl sulfate can also be added to aldehyde surface hybridization reactions to reduce background (Schena, M., "Microarray Analysis, (2003) John Wiley & Sons, New Jersey, p. 117). The target solution may also be contacted with the probe at higher temperatures in order to limit nonspecific interactions.

After the target is contacted with the probe, targets which have not formed target-probe complexes are removed. The unbound targets can be removed through rinsing. Water or an aqueous solution may be used for rinsing away unbound targets.

If the initiator is to be attached through biotin-avidin interaction, a blocking agent can be applied to the microarray to limit nonspecific interaction of avidin. Suitable blocking agents are known to the art and include, but are not limited to, bovine serum albumin (BSA) and nonfat milk. In an embodiment array is incubated with the blocking agent for approximately 20 minutes at about room temperature.

In an embodiment, the target-probe complex is contacted with a photoinitiator label under conditions effective to attach the photoinitiator label to the target probe complex. In an embodiment, the photoinitiator label comprises avidin or streptavidin and at least one photoinitiator. In an embodiment, a plurality of photoinitiators is attached to the avidin or streptavidin to form a polymeric photoinitiator label. In another embodiment, a polymeric photoinitiator label is formed by attaching a plurality of photoinitiators and avidin or streptavidin to a polymer. In an embodiment, the photoinitiators and avidin or streptavidin are attached to the polymer backbone, for example by attachment to subunits in the backbone. The polymer to which the photoinitiators and avidin or streptavidin are attached may be chemically the same or different from the polymer formed during exposure of the polymer precursor solution to light. If the target has been biotin-labeled, interaction between the avidin or streptavidin and the biotin can attach the photoinitiator label to the target, and thus to the target-probe complex. In another embodiment, both the target and the photoinitiator can be labeled with biotin and then multivalent properties of avidin (which can bind four biotins) can be used to bind together the target and the photoinitiator. Information on avidin-biotin interaction is provided in Wilcheck, M., (a) Bayer, E. A. Eds. (1990) "Avidin-biotin technology" *Methods in Enzymology* 184. In an embodiment, the biotin-labeled target-probe complex is contacted with a solution comprising the photoinitiator label for about 20 minutes at room temperature.

Figure 2:
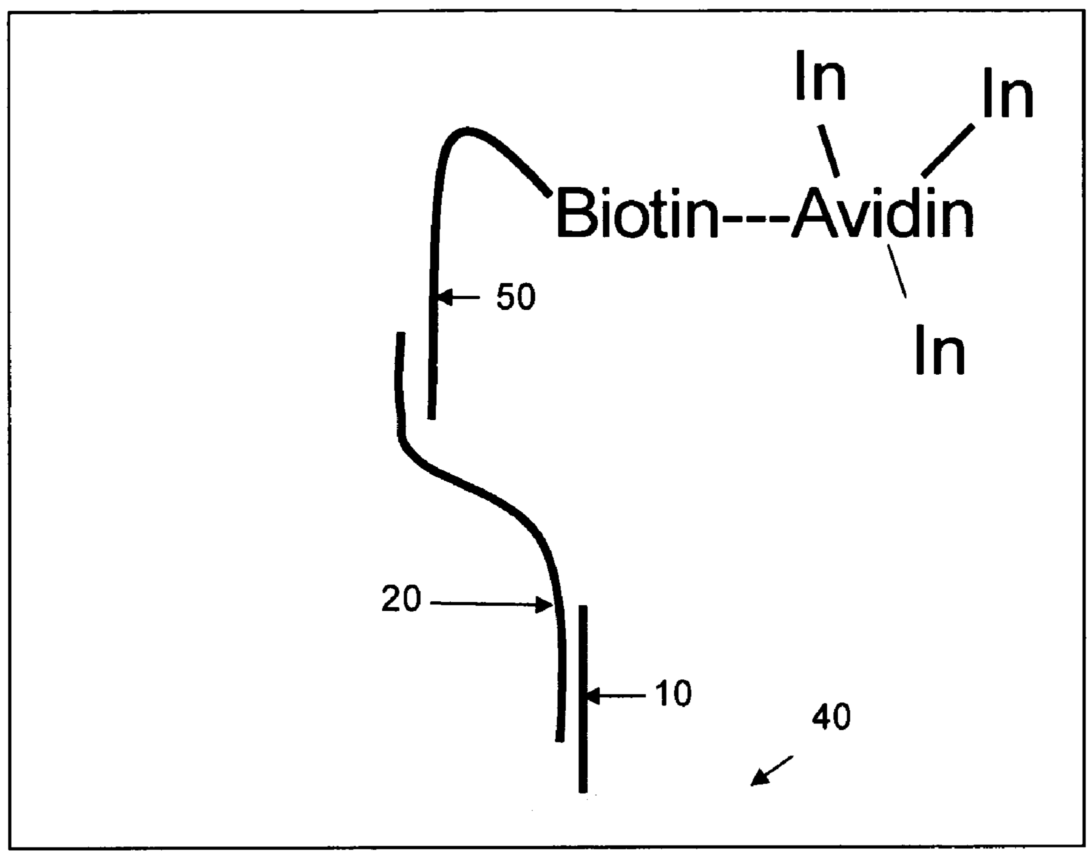
FIG. 2 illustrates an alternate two-step hybridization scheme for detection and amplification.

Another embodiment suitable for hybridization molecular recognition events is schematically illustrated in FIG. 2. In this embodiment, the photoinitiator label (50) comprises a single strand of DNA attached to at least one photoinitiator (In). The photoinitiator can be attached to the ssDNA through biotinylation of the DNA followed by interaction with avidin or streptavidin with at least one photoinitiator attached. In another embodiment, photoinitiators are coupled directly to the end of the oligonucleotide label sequences. Oligonucleotides with 5' amine modifications can be purchased and the reaction conditions in Scheme 2 (EDC coupling) used to form a peptide bond between this amine and the carboxylic acid group of the initiator. The product can be purified by HPLC. During the photopolymerization reaction, the target anchors the initiator, through the label sequence, to the microarray spot. If target viral RNA will not tolerate the presence of the fluorescent monomer and UV light, it is possible to connect the label sequence to the probe oligonucleotide via a treatment with ligase prior to exposure to the photopolymerization reaction conditions. Another method that avoids the use of an enzyme is to place pendant photocrosslinkable groups on the probe oligonucleotide and the label sequence. If, however, the polymerization reaction is fast when compared with the timescale of diffusion, these steps will not be necessary even if the target genetic material detaches from the capture strand.

A number of photoinitiators are known to the art. Photoinitiators that are useful in the invention include those that can be activated with light and initiate polymerization of the polymer precursor. In an embodiment, the photoinitiator is water soluble. Commercially available photoinitiators, for example Irgacure 2959 (Ciba), can be modified to improve their water solubility. In an embodiment, the photoinitiator is a radical photoinitiator. In another embodiment, the photoinitiator is a cationic photoinitiator. In another embodiment, the photoinitiator comprises a carboxylic acid functional group. The photoinitiator is selected to be compatible with the wavelengths of light supplied.

Photoinitiators include azobisisobutyronitrile, peroxides, phenones, ethers, quinones, acids, formates. Cationic initiators include aryldiazonium, diaryliodonium, and triarylsulfonium salts. In an embodiment, the photoinitiator is selected from the group consisting of Rose Bengal (Aldrich), Darocur or Irgacure 2959.(2-hydroxy-1-(4-(hydroxyethoxy)phenyl)-2-methyl-1-propanone, D2959, Ciba-Geigy), Irgacure 651 (2,2-dimethoxy-2-phenylacetophenone, 1651, DMPA, Ciba-Geigy), Irgacure 184 (1-hydroxycyclohexyl phenyl ketone, 1184, Ciba-Geigy), Irgacure 907 (2-methyl-1-(4-(methylthio)phenyl)-2-(4-morpholinyl)-1-propanone, I907, Ciba-Geigy), Camphorquinone (CQ, Aldrich), isopropyl thioxanthone (quantacure ITX, Great Lakes Fine Chemicals LTD., Cheshire, England). CQ is typically used in conjunction with an amine such as ethyl 4-N,N-dimethylaminobenzoate (4EDMAB, Aldrich) or triethanolamine (TEA, Aldrich) to initiate polymerization.

Photoinitiator molecules can be attached to avidin or streptavidin by modification of avidin or streptavidin lysine residues. For photoinitiators having a carboxylic acid functional group, the carboxylic functional group of the photoinitiator can be coupled to the amine of the lysine residue in the presence of a coupling agent. The result is the formation of a peptide bond between the initiator and the protein. Suitable coupling agents are known to those skilled in the art and include, but are not limited to, EDC.

In another embodiment, a polymeric photoinitiator label is formed. Such a polymeric photoinitiator label can be formed from a polymer which can be coupled with both the photoinitiator and a molecular recognition group such as avidin or streptavidin. In an embodiment, the photoinitiator can be attached to the polymer by an ester linkage or by any other kind of linkage known to the art. In an embodiment, the avidin or streptavidin can be attached to the polymer by an amide linkage. In an embodiment, the polymer comprises carboxylic acid groups and amide groups. In an embodiment, the polymer comprises a poly(acrylic acid-co-acrylamide) backbone.

In an embodiment, a polymeric photoinitiator label can be formed from a polymer which comprises one part of a two-part photoinitiator system. The polymer is coupled to a molecular recognition group such as avidin or streptavidin. When the combination of the polymer and the second part of the initiator system is exposed to the appropriate wavelength of light, the initiator system is capable of capable of initiating polymerization of a polymer precursor. In an embodiment, one part of the two-part photoinitiator system is a tertiary amine which is part of the polymeric photoinitiator label. The other part of the photoinitiator system can be camphorquinone. (CQ) This two-part system can be activated by light of approximately 469 nm. The tertiary amine can be incorporated into the polymer label by co-polymerizing acrylic acid with a monomer comprising the tertiary amine and an acrylate group.

In an embodiment, the polymeric photoinitiator comprises sufficient photoinitiators so that it may be regarded as a macroinitiator (having many initiators present on a single molecule). The number of initiator groups per molecule or chain may vary from one chain to another. In an embodiment, the use of a macroinitiator can increase the average initiator concentration by a factor of between about 10 to about 100. In another embodiment, the average number of initiators per polymer chain is between about 100 and about 200. In another embodiment, the average number of initiators per polymer chain is between about 120 and about 160. The number of molecular recognition groups may also vary from chain to chain. In an embodiment, the average number of molecular recognition groups is between one and three. Without wishing to be bound by any particular belief, it is believed that the incorporation of too many initiator groups can lead to nonspecific interaction between the macroinitiator and the array. The molecular weight of the backbone polymer is selected to be large enough to allow attachment of the appropriate number of initiator and molecular recognition groups. For a poly(acrylic acid-co-acrylamide) backbone, the molecular weight of the backbone is preferably greater than about 50,000.

After contact of the photoinitiator label with the target-probe complex, unattached photoinitiator is removed. Unattached photoinitiator may be removed by rinsing with water or an aqueous solution.

In an embodiment, the photoinitiator-labeled target-probe complex is contacted with a solution comprising a polymer precursor. As used herein a "polymer precursor" means a molecule or portion thereof which can be polymerized to form a polymer or copolymer. Polymer precursors include any substance that contains an unsaturated moiety or other functionality that can be used in chain polymerization, or other moiety that may be polymerized in other ways. Such precursors include monomers and oligomers. In an embodiment, the solution further comprises a solvent for the polymer precursor. In an embodiment, the solvent is aqueous.

In an embodiment, the amount of oxygen dissolved in the polymer precursor solution is minimized to minimize oxygen inhibition of the polymerization process. In an embodiment, the oxygen content of the solution is less than about $1\times10^{-5}$ moles/liter. The amount of oxygen dissolved in the solution may be minimized by control of the atmosphere under which polymerization takes place, reducing the oxygen content of the polymer precursor solution by flowing a gas through it and/or the addition of oxygen inhibition agents. In an embodiment, oxygen inhibition agents such as multifunctional thiol reagents are not used. In an embodiment, the oxygen content of the polymer precursor solution during polymerization can be minimized by performing the polymerization in an enclosure and introducing a gas which does not have a substantial oxygen content into the enclosure. In different embodiment, the oxygen content of the gas is less than about 10%, less than about 5% and less than about 1%. Suitable gases include, but are not limited to, commercial purity argon and nitrogen. The atmosphere in the enclosure may be obtained by simply filling the enclosure with the desired gas, or by flowing gas through the enclosure. The enclosure can also be evacuated and backfilled with gas. The oxygen content of the polymer precursor solution can also be reduced prior to polymerization by bubbling a suitable gas through the solution, or by any other method known in the art. Suitable gases include those which do not have a substantial oxygen content, such as argon and nitrogen.

The solution may further comprise oxygen inhibition agents and/or cross-linking agents. In an embodiment, the oxygen inhibition agent is a multithiol (Bhanu, V. A. & Kishore, K. (1991) Role of Oxygen in Polymerization Reactions, *Chemical Reviews* 91: 99-117). The amount of oxygen inhibition agent should not be so much that polymerization occurs in the bulk of the solution rather than from the surface. However, oxygen inhibition agents which can act as chain transfer agents are not recommended for use with radical polymerization processes when it is desired to form sufficient quantities of the polymer for visual detection. A crosslinking agent can stabilize the polymer that is formed and improve the amplification factor (Hacioglu B., Berchtold K. A., Lovell L. G., Nie J., & Bowman C. N. (2002) Polymerization Kinetics of HEMA/DEGDMA: using Changes in initiation and Chain Transfer Rates to Explore the Effects of Chain-Length-Dependent Termination. *Biomaterials* 23:4057-4064). Finally, a small amount of inhibitor can be added to the formulation to limit background polymerization caused by impurities and trace radicals formed by absorption by molecules other than the initiator.

In different embodiments, the polymer precursor is a photopolymerizable monomer capable of forming a fluorescent polymer, a magnetic polymer, a radioactive polymer or an electrically conducting polymer. In an embodiment, the polymer precursor is water soluble. In an embodiment, the polymer precursor is a photopolymerizable fluorescent methacrylate monomer. When the polymer precursor is fluorescent, the fluorophore may absorb the light used in the photopolymerization process. To compensate, the exposure time of the polymer precursor to the light and/or the light intensity can be adjusted. In another embodiment, the polymer precursor need not be capable of forming a fluorescent, magnetic, radioactive or electrically conducting polymer if sufficient quantities of the polymer can be formed. In this embodiment, the polymer precursor can be any photopolymerizable polymer precursor or monomer. In an embodiment, the polymer precursor can be an acrylate or a mixture of acrylates. The polymer precursor can also comprise a chromophore. In an embodiment, the photoinitiator and chromophore preferentially absorb different wavelengths of light.

In another embodiment, the polymer precursor is capable of forming a polymer gel. In an embodiment, the gel is covalently crosslinked and a cross-linking agent is added to the polymer precursor containing solution. In another embodiment, the gel is noncovalently crosslinked. In an embodiment, the polymer gel formed is not substantially fluorescent, magnetic, radioactive, or electrically conducting. Instead, detection can occur through absorption of a fluorescent, magnetic, radioactive, or electrically conducting solution by the gel. Detection can also occur through visual inspection of the quantity of gel formed is sufficiently large.

In an embodiment, the polymer gel is a hydrogel. The term "hydrogel" refers to a class of polymeric materials which are extensively swollen in an aqueous medium, but which do not dissolve in water. In general terms, hydrogels are prepared by polymerization of a hydrophilic monomer under conditions where the polymer becomes cross-linked in a three dimensional matrix sufficient to gel the solution. The hydrogel may be natural or synthetic. A wide variety of hydrogel-forming compositions are known to the art. In an embodiment, the monomer used to form the hydrogel is selected from the group consisting of acrylates, methacrylates, acrylamides, methacrylamides, cyclic lactams and monomers with ionic functionality. Monomers with ionic functionality include methacrylate, methacrylamide, and styrene based monomers with acidic or basic functionality. In an embodiment, the monomer used to form the hydrogel is an acrylate or methacrylate. In another embodiment, the hydrogel-forming monomer is selected from the group consisting of polysaccharides and proteins. Polysaccharides capable of forming hydrogels include alginate, chitin, chitosan, cellulose, oligopeptides, and hyalauric acids. Proteins capable of forming hydrogels include albumin and gelatin. Suitable acrylate mixtures for hydrogel formation include, but are not limited to, mixtures of hydroxyethyl acrylate (HEA) and elthylene glycol dimaethacylate (EGDMA). In an embodiment, the monomer is hydroxyl ethyl acrylate (HEA).

The photoinitiator-labeled target-probe complex and polymer precursor are exposed to light, thereby forming a polymer. Photopolymerization occurs when polymer precursor solutions are exposed to light of sufficient power and of a wavelength capable of initiating polymerization. The wavelengths and power of light useful to initiate polymerization depends on the initiator used. Light used in the invention includes any wavelength and power capable of initiating polymerization. Preferred wavelengths of light include ultraviolet or visible. Any suitable source may be used, including laser sources. The source may be broadband or narrowband, or a combination. The light source may provide continuous or pulsed light during the process. Both the length of time the system is exposed to UV light and the intensity of the UV light can be varied to determine the ideal reaction conditions. For fluorescence detection, the exposure time and light intensity can be varied to obtain maximal fluorescence signal from spots on a microarray and minimal fluorescence signal from the background. In an embodiment, the intensity of UV radiation is selected so that an appropriate dose of UV radiation can be delivered in less than about one-half hour.

In an embodiment, after polymerization, unpolymerized polymer precursor is removed. The unpolymerized polymer precursor can be removed by rinsing, for example by rinsing with water or an aqueous solution. The unpolymerized polymer precursor need not be removed if formation of the polymer is to be detected by its refractive index or by other means that would not be interfered with by the presence of the unpolymerized polymer precursors.

If the hydrogel polymer is not substantially fluorescent, magnetic, radioactive, or electrically conducting, the hydrogel can be contacted with a detectable solution which is fluorescent, magnetic, radioactive, or electrically conducting so that the hydrogel absorbs a sufficient quantity of the detectable solution. After the detectable solution is absorbed into the hydrogel, the excess solution is removed before detection.

In an embodiment, the polymer formed is detected by fluorescence, magnetic, radioactive or electrical detection methods as are known to the art. If the probes are part of a DNA microarray, a commercially available microarray scanner and/or imager can be used to detect polymer formation. DNA microarray scanners and/or imagers are commercially available that can detect fluorescent or radioisotopic labels.

In another embodiment, sufficient quantities of the polymer are formed that polymerization can be detected by visual inspection. Polymerization which is detectable by visual inspection may also be detectable via image analysis of photographs or digital images of part or all of the array or substrate. Polymerization can be detected by visual inspection when there is sufficient contrast between the areas where polymer has formed and the unpolymerized monomer, the other areas of the array or the array substrate. In an embodiment, the areas where the polymer has formed appear to be a different color (or shade of gray) than the unpolymerized monomer, the other areas of the array or the array substrate. For example, after unpolymerized monomer is removed, the areas where polymer has formed may appear darker than the array substrate. In another embodiment, the areas where the polymer has formed can have a different transparency than the unpolymerized polymer precursor. For example, the unpolymerized polymer precursor may be clear and the polymer more opaque and whitish in color. The amount of polymer required for visual detection of polymer formation may depend upon the polymer. For acrylate mixtures such as mixtures of Hydroxyethyl Acrylate (HEA) and Ethylene Glycol Dimethacrylate (EGDMA), the thickness of the polymer formed can be greater than about 1 micron, or greater than about 5 microns.

Analysis of polymer formation can allow identification of the target. Methods of design and analysis of DNA microarrays for identification of target molecules are known to the art (Vernet, G. (2002) "DNA-Chip Technology and Infectious Diseases" Virus Research 82:65-71). Similar methods, appropriately modified, can be applied to other types of microarrays and molecular recognition events.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and subranges, as well as all individual values included in the ranges given are intended to be included in the disclosure. When a Markush group or other grouping is used herein, all individual members of the group and all combinations and subcombinations possible of the group are intended to be individually included in the disclosure.

In general the terms and phrases used herein have their art-recognized meaning, which can be found by reference to standard texts, journal references and contexts known to those skilled in the art. The above definitions are provided to clarify their specific use in the context of the invention.

All patents and publications mentioned in the specification are indicative of the levels of skill of those skilled in the art to which the invention pertains.

All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

EXAMPLE 1

Synthesis of a Water Soluble Initiator

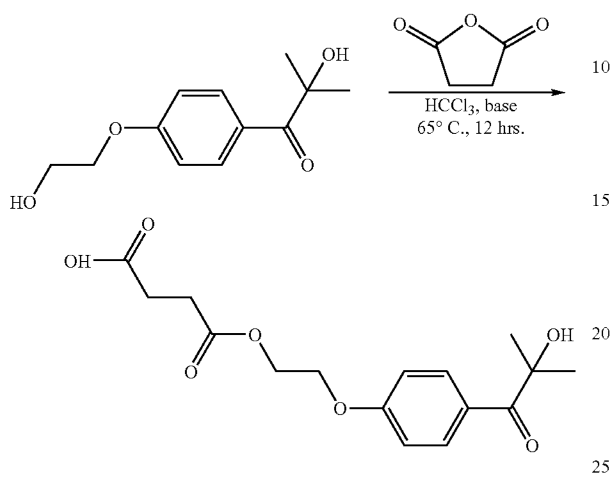

As shown in Scheme 1, synthesis of a water soluble photoinitiator (preferred for compatibility with a BioChip) was achieved by starting with commercially available Irgacure 2959 (left most structure, Ciba Specialty Chemicals (http://www.cibasc.com)). Irgacure 2959 was dissolved/suspended in chloroform along with succinic anhydride and a catalytic amount of 4-dimethylaminopyridine. The solution was refluxed, with stirring, for 12 hours at 65° C. In both chloroform and water, the product was soluble while the starting materials were sparingly soluble. The product structure was verified by NMR and shown to function as a photoinitiator by monitoring the double bond conversion of an acrylate monomer using time-resolved FTIR.

EXAMPLE 2

Functionalization of Avidin with Photoinitiator

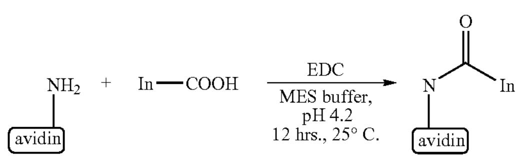

Avidin is often labeled with dye molecules by modification of its many lysine residues (for example, Pierce Biotechnology sells a kit for this purpose). These types of modifications do not disrupt avidin's ability to bind to biotin (Wilbur, D. S.; Hamlin, D. K.; Buhler, K. R.; Pathare, P. M.; Vessella, R. L.; Stayton, P. S.; To, R. (1998) "Streptavidin in antibody pretargeting. 2. Evaluation of methods for decreasing localization of streptavidin to kidney while retaining its tumor binding capacity" *Bioconjugate Chemistry* 9: 322-330). Here, as shown in Scheme 2, the lysine residues have been modified with a photoinitiator (rather than a dye) by coupling the carboxylic acid functional group of the photoinitiator to the amine of the lysine residue. The result is formation of a peptide bond between the initiator and the protein. Avidin and an excess of the initiator (the product in Scheme 1, represented by In in Scheme 2) were dissolved in an acid aqueous buffered solution in the presence of the water-soluble coupling agent 1-ethyl-3-(3-dimethylaminopropyl) carbodiimide (EDC) (Hermanson, G. T. (1996) *Bioconjugate Techniques* San Diego, Calif.: Academic Press. p. 435). The reaction proceeded at room temperature for 12 hours, and the product was collected by ultracentrifugation through a 3,000 MW cutoff filter. Biotin binding capabilities were verified using the HABA assay (Wilcheck, M., (b) Bayer, E. A. Eds. (1990) "Protein biotinylation" *Methods in Enzymology* 184: 138-160).

EXAMPLE 3

Synthesis of a Polymer Labeled with Photoinitiator and Streptavidin

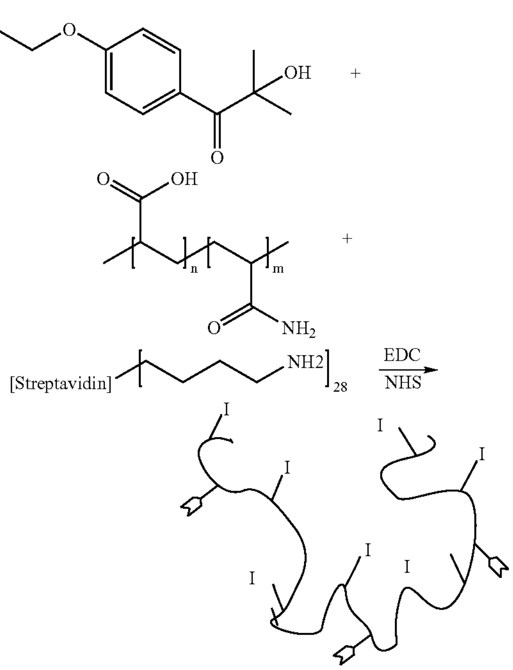

Scheme 3 illustrates the formation of a polymer labeled with Irgacure 2959 photoinitiator (denoted by I) and streptavidin (denoted by ➘).

Macroinitiators were synthesized using poly(acrylic acid-co-acrylamide) (MW=200,000 g/mol), Irgacure 2959, and streptavidin as starting materials. The water-soluble coupling agent 1-ethyl-3-[3-dimethylaminopropyl]carbodiimide (EDC) and the intermediate-stabilizing molecule N-hydroxsuccinimide (NHS) were used to create amide linkages between some of the acrylic acid subunits and streptavidin and to create ester linkages between other acrylic acid subunits and the initiator Irgacure 2959 (12959). Still other acrylic acid subunits were left unmodified to assure the water solubility of the resulting macroinitiator. Two types of reaction conditions were varied in order to change the number of initiators that coupled per chain. First, the stoichiometry of reactants was varied up to the limit of solubility of the initiator in the aqueous conjugation buffer.

Second, the length of time allowed for the activation step (in which EDC and NHS react with the carboxylic acid subunits of poly(acrylic acid-co-acrylamide)) was varied. Table 1 summarizes results from three sets of reaction conditions.

TABLE 1

| | Stoichiometry | Activation time | Absorbance at 300 | Initiators per chain* |
|---|---|---|---|---|
| 1 | 685 µL of 1 mg/ml I2959<br>440 µL of 1 mg/ml EDC<br>260 uL of 1 mg/ml NHS | 10 minutes | 0.8 | 140 |
| 2 | 685 µL of 1 mg/ml I2959<br>440 µL of 1 mg/ml EDC<br>260 uL of 1 mg/ml NHS | 15 minutes | 1.3 | 40 |
| 3** | 68.5 µL of 1 mg/ml I2959<br>44 µL of 1 mg/ml EDC<br>26 uL of 1 mg/ml NHS | 15 minutes | 0.5 | 88 |

*Calculated using a standard curve of absorbance at 300 of the initiator as a function of initiator concentration.
**Reaction 3 was brought up to equal volume with Reactions 1 and 2 using the conjugation buffer.

After activation, the initiator and protein are added and the reaction takes place in the presence of EDC and N-hydroxysuccinimide (NHS) at room temperature for about two hours.

EXAMPLE 4

Macroinitiator Synthesis

In the event that a label sequence containing a single initiator does not provide a high enough level of amplification with the short irradiation times necessary to minimize background fluorescence, macroinitiators, in which many initiators are present on a single molecule, can be used. Synthesis of a macroinitiator can be achieved through a living (or controlled) radical polymerization method prior to utilization on the microarrays (Kamigaito M., Ando T., & Sawamoto M. (2001) "Metal-Catalyzed Living Radical polymerization. *Chemical Reviews* 101: 3689-3746). Atom transfer radical polymerization (ATRP) schemes can be used to control the macroinitiator molecular weight, composition and architecture (block copolymers, branching, etc.) (Matyjaszewski, K. & Jianhui Xia, J. (2001) Atom Transfer Radical Polymerization *Chemical Reviews* 101: 2921-2990).

Macroinitiator synthesis can be performed, as presented in Scheme 4, by starting with an oligonucleotide terminated in an amine group. The amine terminus is functionalized with an ATRP initiator, which initiates polymerization of the desired compounds. As many as three different monomers (an initiator, a spacer, and a photosensitizer) may need to be copolymerized. If necessary to improve hybridization to the probe oligonucleotide, a spacer molecule (for example (poly ethylene glycol methacrylate)) is used between the initiating block of the macroinitiator and the oligonucleotide part of the label sequence. The spacer may also be used for controlling solubility of the macroinitiator (by changing the hydrophobicity/hydrophilicity) and the macroinitiator molecular weight.

Scheme 4. Reaction for generation of macroinitiator.

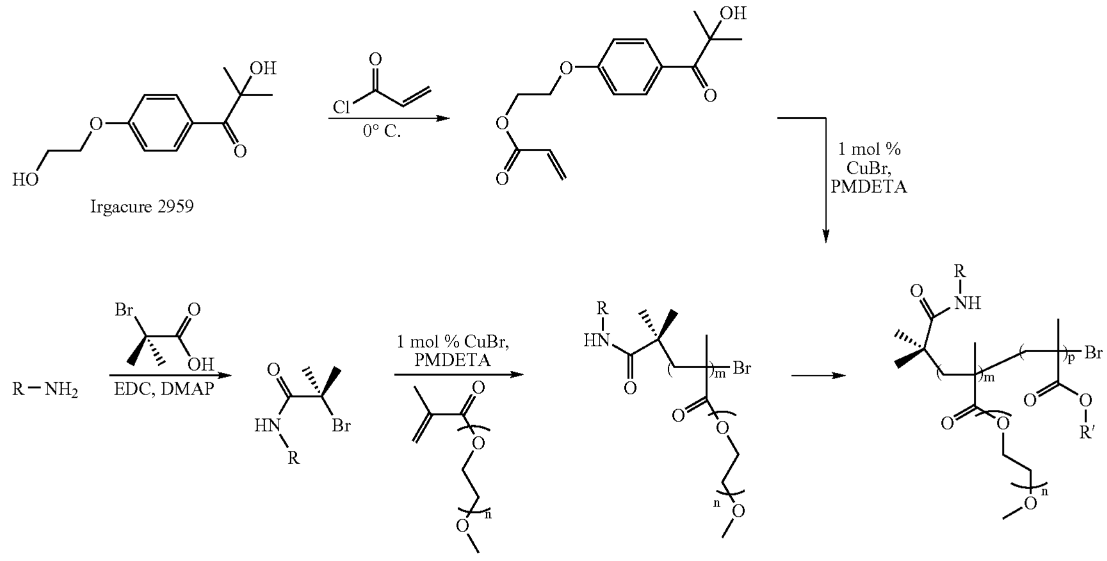

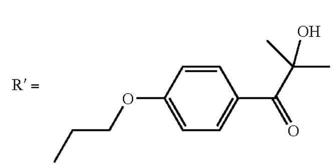

Photosensitizing components are incorporated into the macroinitiator in systems where minimization of the background polymerization is necessary.

EXAMPLE 5

Synthesis and Photopolymerization of a Fluorescent Monomer

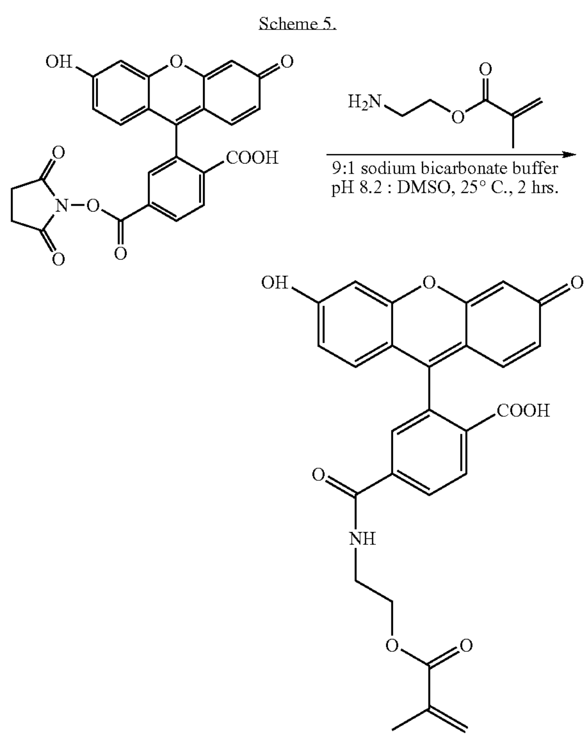

The N-hydroxy succinimide ester of fluorescein was purchased from Pierce Biotechnology (Rockford, Ill.) and 2 mg were dissolved in 100 μL of DMSO while 0.5 mg of 2-aminoethyl methacrylate was dissolved in 900 μL of sodium bicarbonate buffer, pH 8.2. The two solutions were combined and placed on a shaker for two hours. The solvent was lyophilized off. The structures of the fluorescent monomer and the polymer that results from irradiating the monomer with UV light were verified by NMR.

The monomer can be polymerized by irradiating with 365 nm ultraviolet light for one minute.

EXAMPLE 6

Formation of a Hydrogel from a Polymer Labeled with Photoinitiator and Streptavidin and Detection of the Hydrogel Formed The polymer of Example 3 was reacted with a microarray having biotin covalently bound to the microarray substrate. A hydroxyl ethyl acrylate monomer solution was placed in contact with the array by pipetting the solution into a HybriWell (Grace Biolabs) which covers the array. Sixty μl of an aqueous solution was used which contained hydroxyl ethyl acrylate, initiator (product of Scheme 1 and Scheme 3), cross-linking agent (ethylene glycol dimethacrylate, 3% by volume), and oxygen inhibition agent (mercaptoethanol, $5\times10^{-4}$% by volume).

The monomer was then photopolymerized to form a hydrogel by irradiating the array with 365 nm light for about 1 minute.

After polymerization, the microarray was rinsed with water and then a solution containing Rhodamine B, concentration 100 nM, was pipetted between a glass coverslip and the microarray. The microarray was exposed to the fluorophore containing solution for about 30 minutes. The microarray was then rinsed with water to remove excess fluorophore.

Figure 3A:
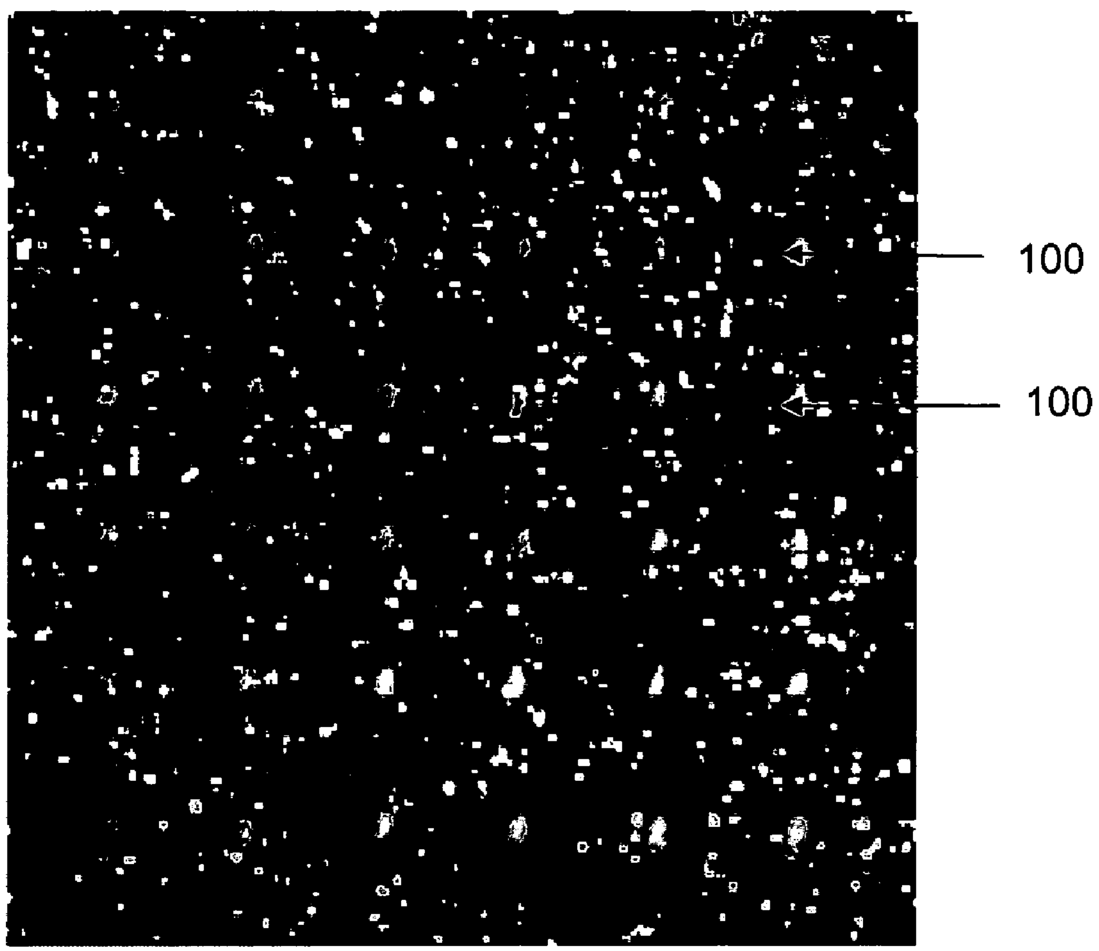
FIGS. 3A and 3B illustrate fluorescence detection of macroinitiators on a biotin array.
Figure 3B:
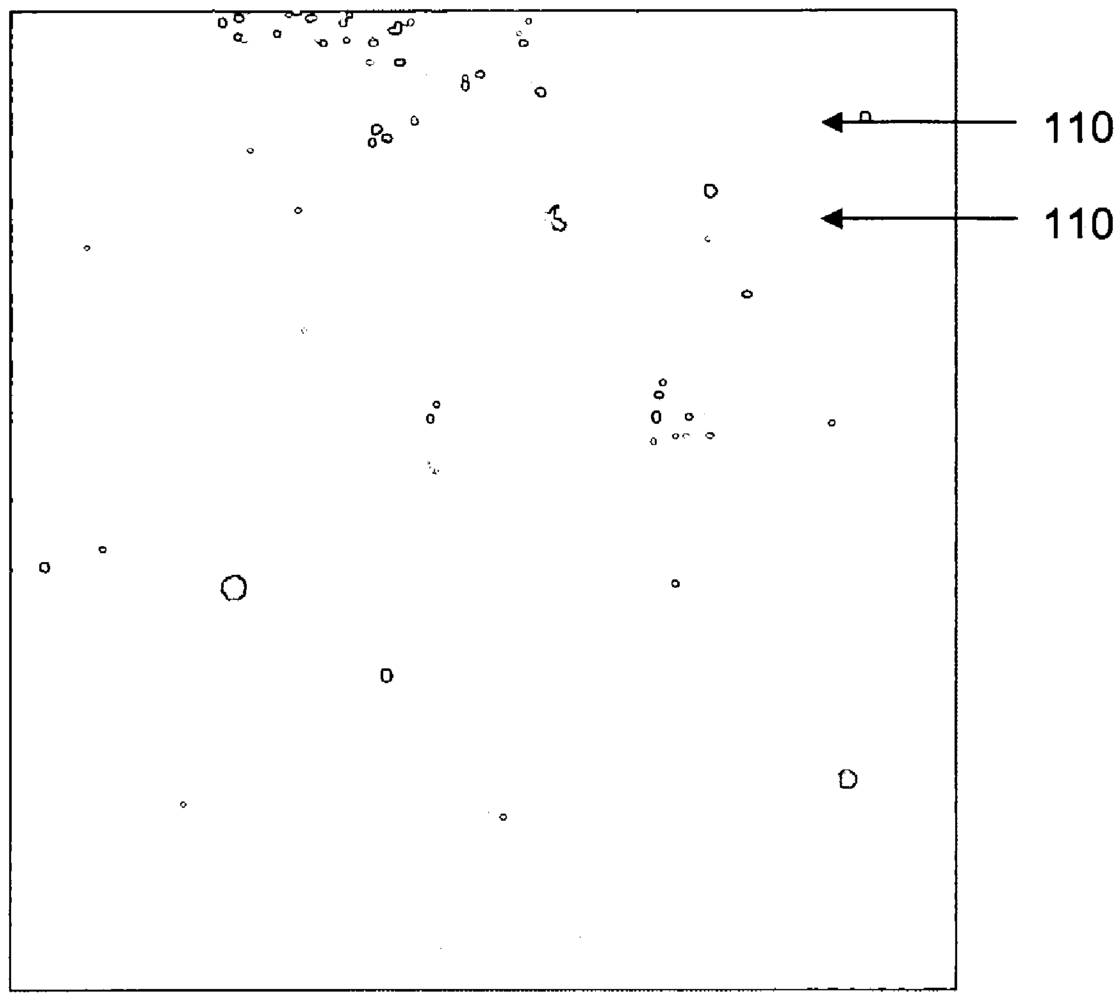

FIG. 3A is an image of the array after polymerization. The grid of reacted biotin spots (100) are bright and indicate areas of formation of hydrogel swollen with the fluorescent solution. The detector used was an Agilent Microarray Scanner (Fluorescence Ave: 2600, Std: 1200 Background: 1200Signal to Noise: 2.2). FIG. 3B shows negative controls spots (110) on the same array (Fluorescence Ave: 900, Std: 30, Background: 800, Signal to Noise: 1.1)

EXAMPLE 7

On-Chip Hybridization, Amplification, and Detection on a Flu Chip

Figure 4:
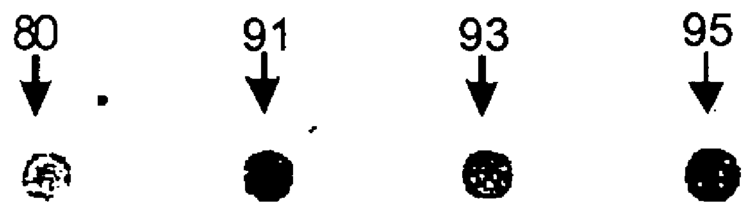
FIG. 4 illustrates an image of a FluChip developed using photopolymerization for signal enhancement.

On-chip signal amplification by photopolymerization was tested on a custom microarray designed to detect and subtype the influenza virus. As shown in FIG. 4, the chip had a column of positive control spots (80), spots to capture RNA of influenza C (91), spots to capture RNA of influenza B (93), and spots to capture RNA of influenza A (95). There were three spots in each column. The sequence that is complementary to the positive control spots (but not to the other nine spots on the array) was purchased from Qiagen (Valencia, Calif.) with a 5' biotin modification. Published protocols were used to hybridize a 1 μM solution of this oligonucleotide to the microarray. The hybridization procedure was as follows:

Pre-hybridization.

1. Boil $dH_2O$.
2. While $dH_2O$ is boiling, wash microarray in 0.1% sodium dodecyl sulfate (SDS) for 2-10 min on rocker. (0.5 ml 10% SDS in 50 ml total volume).
3. Transfer to 2× standard saline citrate (SSC) for 2 min. (5 ml 20× in 50 ml total volume).
4. Immerse slide in boiling/hot (>95° C.) water for 2-3 min.
5. Remove slide, blot on kimwipe.
6. Immerse slide in ice-cold ethanol bath for 2-5 min. Store EtOH at −20° C.
7. Remove slide, blot on kimwipe.
8. Centrifuge ethanol off of slide. (50 ml conical tube, 1000 rpm, 3 min).

Hybridization.

1. Pipette 10 μL of water or buffer into the humidification slots, place microarray in hybridization cassette.
2. Hybridization solution:
   10 μL 50 micromolar oligo soln (phosphate-buffered saline (PBS) or tris(hydroxymethyl) aminomethane (Tris))
   10 μL 10×SSC
   5 μL 1% Tween 20 (polyoxyethylene-20-sorbitan monolaurate, ICI)
   5 μL 10
   mM $MgCl_2$
   20 μL $H_2O$ 3. Pipette 7 μL of this solution between a coverslip covering the microarray and the slide.
4. Seal cassette, submerge in water bath (40-45° C.) for at least 1.5-2 hrs.

Washing.

1. Transfer microarray immediately into 1×SSC (2.5 ml 20× in 50 ml total)/0.1% SDS (0.5 ml 10% SDS in 50 ml total). 5 min.
2. Transfer microarray into 0.1×SSC (0.25 ml 20× in 50 ml)/0.1% SDS. 5 min.
3. Immerse briefly in 0.1×SSC to remove SDS.

Rinse with water, dry with $N_2$.

Following hybridization, 7 μL of a 1 mg/ml solution of BSA was pipetted between a glass coverslip and the microarray to block nonspecific binding. Following twenty minutes of incubation in a humid hybridization chamber, the array was rinsed with water. Subsequently, 7 μL of a 1 mg/ml initiator-functionalized avidin solution was pipetted between a glass coverslip and the microarray. After twenty minutes of incubation and brief rinsing with water, 7 μL of a saturated solution of the fluorescent monomer in water was pipetted between the glass coverslip and the microarray. The array was irradiated with 365 nm UV light for one minute, rinsed with water, and imaged using an Agilent (Wilmington, Del.) microarray scanner. The excitation wavelength ($\lambda_{ex}$=532 nm) and collection wavelength (centered at 575 nm) were not optimal for the fluorescein derivative (product in Scheme 3). FIG. 4 is the resulting image In FIG. 4, the lighter spots represent detected fluorescence. Though the background fluorescence remains relatively high despite the BSA treatment, the positive control spots (80) are definitely more fluorescent than the spots designed to capture the genetic material of influenza A, B and C (these spots effectively served as three different negative controls in this experiment). The faint gray vertical lines in FIG. 4 are a well understood artifact. Glass slides were placed between the microarray and the UV light source to block high frequency UV light that is harmful to the fluorophore. The vertical lines arise from the seam between two glass slides that were used as a filter in this manner.

Two other control experiments were performed. Without the BSA nonspecific binding blocking step, and all other steps held constant, the entire image yielded significant fluorescence, indicating nonspecific binding of the initiator. In addition, without the addition of avidin-functionalized initiator, when all other steps remained identical, none of the spots exhibited fluorescence yet the background was still high. These results suggest that the fluorescent spots in FIG. 4 do indeed result from an interaction between the monomer and the selectively bound initiator. These tests, taken together, indicate that photopolymerization is clearly a viable means to obtain selective signal amplification directly on a DNA microarray.

Without wishing to be bound by any specific theory, one possible cause of nonspecific binding is reaction of the fluorescent monomer with the aldehyde coating on the glass. To eliminate this source of nonspecific binding, alternative attachment chemistries are available, or the unreacted aldehydes outside of the oligonucleotide spots can be passivated or reduced. If macroinitiators containing larger numbers of initiators are used, the irradiation time can be reduced. To further reduce nonspecific binding, an inhibitor can be included. This technique will be effective if the number of initiation sites inside the hybridized spots (specific, due to the presence of many initiators) is much greater than the number of possible sites outside the spots (nonspecific, absorption and initiation occurring without initiator, and non-specific binding). False positives can be minimized by the use of macroinitiators, photosensitizers/inhibitors and optimal initiation time and light intensity, combined with judicious choice of probe and label sequence and steps to prevent non-specific binding of the initiator to the array

EXAMPLE 8

Quantification of Number of Fluors

The number of fluorescent molecules incorporated into the polymer and therefore bound to the microarray surface can be quantified. One test is to measure the shape and size of the resulting spot after polymerization is complete using either atomic force microscopy or profilometry. With this information and knowledge of the mass fraction of fluor within the mixture and the polymer density, it is possible to calculate relatively accurately the number of fluors within the polymer. This approach minimizes error due to any fluorescence quenching within the polymer. Quenching is quantified and minimized by conducting a study of fluorescence intensity as a function of mass percent fluor in the polymer. Due to the amorphous nature of the polymer, quenching is not expected to be significant.

EXAMPLE 9

Recognition Between Biotin Arrays and Polymers Functionalized with Streptavidin and Photoinitiator A biotin array was contacted with a macroinitiator solution comprising a poly (acrylic acid-co-acrylamide) polymer backbone (MW=200,000) functionalized with streptavidin and Irgacure 2959. The reaction conditions for forming the macroinitiator were as given in Table 1. The array was then washed to remove macroinitiator not attached to the biotin array. The photoinitiator-labeled array was then contacted with a monomer solution comprising Hydroxyethyl Acrylate (HEA) and Ethylene Glycol Dimethacrylate (EGDMA). The monomer solution had been previously purged with argon to reduce its oxygen content. The photoinitiator labeled array and monomer solution were then exposed to 5 mW/cm$^2$, 365 nm UV light for 20 minutes in an argon atmosphere. Unpolymerized monomer solution was then removed by washing. Details of biotin array preparation, monomer preparation, recognition and amplification procedures are given below.

Figure 5:
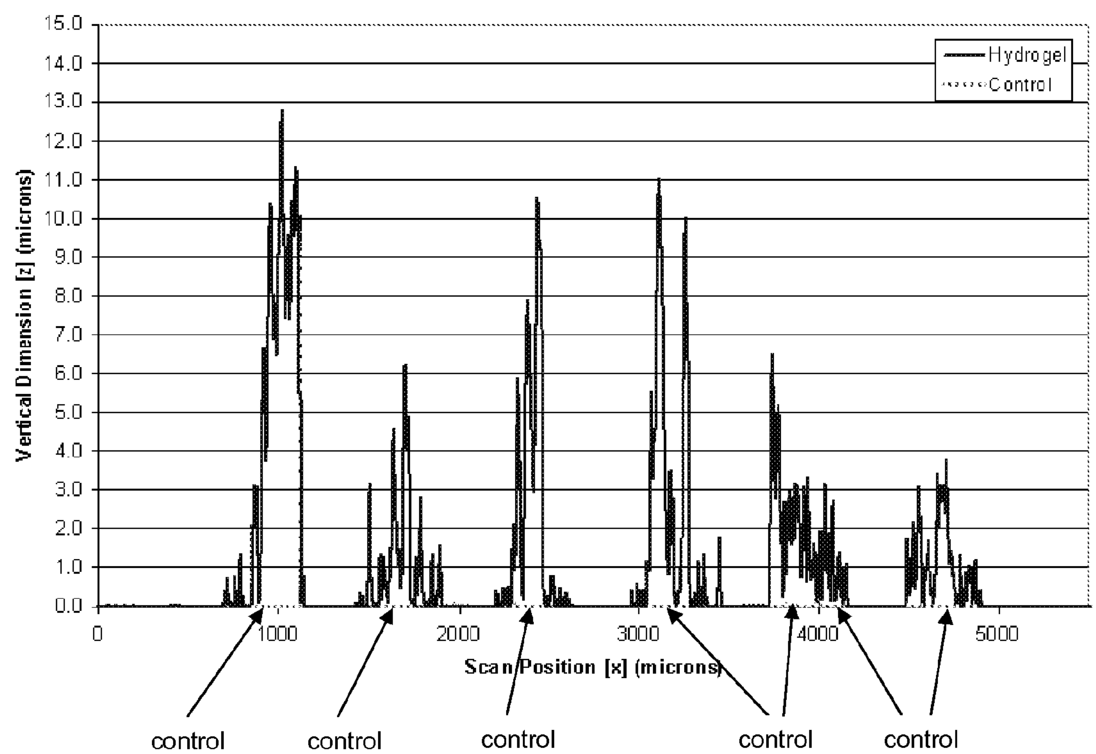
FIG. 5 shows a profilometry scan across a row of polymer spots that were grown from an array following recognition of biotin by a streptavidin macrophotoinitiator.

The product of reaction 1 (see Table 1) led to the formation of polymer spots that were up to 10 microns thick, as measured with a profilometer. FIG. 5 compares a profilometer trace across the hydrogel spots with a control profilometer trace. A digital image of the polymer spots shows that they are darker than the surrounding substrate. The product of reaction 2 led to polymerization everywhere (not just within the spots). The product of reaction 3 led to the formation of polymer spots that were up to 0.1 micron thick, as measured using a profilometer.

Biotin Array Preparation:

1. Vapor-deposit aminopropyltriethoxysilane onto a piranha cleaned silicon (or glass) substrate. Piranha cleaning involves placing substrates in 70% v/v sulfuric acid, 30% v/v 30% hydrogen peroxide at 90oC for 1 hour. Vapor deposition includes placing substrates into a purged Teflon container along with an open vial containing the silane for two hours at 90° C.

2. Spot 1 mg/mL biotin-polyethylene glycol (PEG)-benzophenone in 1× PBS on an amine substrate. Set relative humidity in spotter to 75%. Allow substrates to dry in spotter for half hour after spotting is complete and then move to ambient conditions to dry for at least 2 hrs.
3. Covalent attachment of biotin to the surface: irradiate the substrate with UV light at 5 mW/cm2 using Black Ray lamp at 365 nm for 10 minutes.
4. Blocking of nonspecific binding: soak arrays in 1 mg/mL dry milk in water solution for two hours while slowly agitating with shaker.
5. Wash arrays ×3 in water for 5 minutes, then dry the slides using a stream of nitrogen.

Monomer Preparation:

1. Hydroxyethyl Acrylate (HEA) and Ethylene Glycol Dimethacrylate. (EGDMA) are deinhibited from MEHQ by three consecutive distillations.
2. Make 300 μL of 97 vol % HEA and 3 vol % EGDMA.
3. Purge monomer of dissolved oxygen by bubbling argon through the monomer for 10 minutes and then seal the container with Parafilm® when done.

Recognition:

1. Pipette a 20 μL of macrophotoinitiator solution (1.4 mg poly (acrylic acid-co-acrylamide backbone per ml in 0.1 M 2-(N-morpholino) ethane sulfonic acid (MES) buffer, 0.5 M NaCl, pH 5) directly onto array and then drop a plastic coverslip onto drop, making sure drop spreads uniformly over coverslip area. Place slide in humid chamber for 20 minutes.
2. Wash slide ×3 in water for 5 minutes, do not dry slide with nitrogen.

Amplification:

1. Place silicone isolator around spots, making sure it adheres to the plate well. This will keep the monomer from spreading everywhere on the substrate.
2. Place plate in argon chamber and then pipette 300 μL of monomer inside the well formed by the isolator and the substrate.
3. Put glass top on chamber, turn argon on, let it purge for 5 minutes. After 5 minutes, tighten down the top on the chamber.
4. Irradiate the plate in the chamber for 20 minutes under 5 $mW/cm^2$, 365 nm UV light.
5. Remove plate from purge chamber and wash ×3 in water, dry with nitrogen. Look for polymer spots that have grown from the array.

EXAMPLE 10

Polymerization of a Chromophore-Containing Monomer Using a Macroinitiator Incorporating Tertiary Amines A chromophore-containing monomer is polymerized using a photoinitiator which preferentially absorbs light at a different wavelength than the chromophore. A chromophore which preferentially absorbs UV light can be paired with a photoinitiator which preferentially absorbs visible light. Scheme 6 illustrates formation of an acrylate monomer incorporating the chromophore Cascade Blue Ethylene Diamine, which preferentially absorbs light at approximately 400 nm. Scheme 7 illustrates formation of a macroinitiator comprising a polymer incorporating multiple tertiary amines. The photoinitiator for the polymerization of the monomer comprising the tertiary amine and the acrylate group with acrylic acid is (for water solubility and to provide a functional group that streptavidin can be coupled to) Irgacure 184. 1-hydroxycyclohexyl phenyl ketone (Ciba-Geigy). The polymer chain is coupled to at least one molecular recognition group, shown as streptavidin in Scheme 7. As shown in Scheme 8, the tertiary amines of the macroinitiator and CQ form a two-part initiator system which most strongly absorbs light at 469 nm. The radical species shown in Scheme 8 propagates through the carbon-carbon double bonds of the chromogenic monomer that is the product of Scheme 6 to form a chromogenic monomer.

Scheme 6:

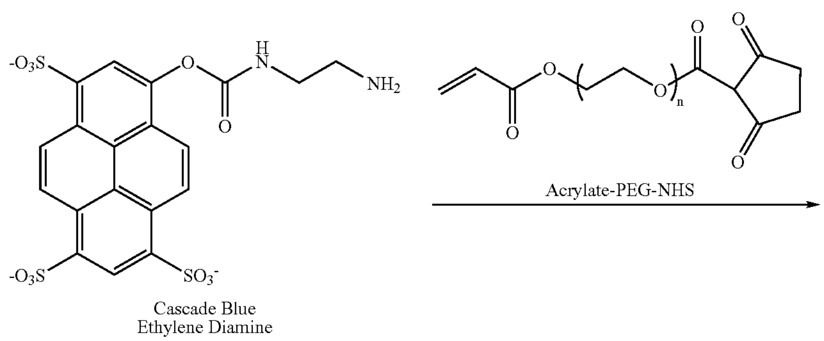

-continued

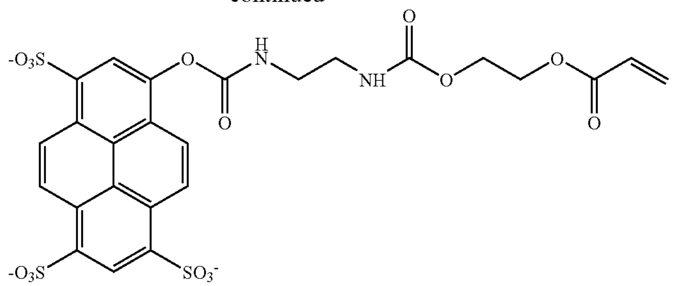

Scheme 7:

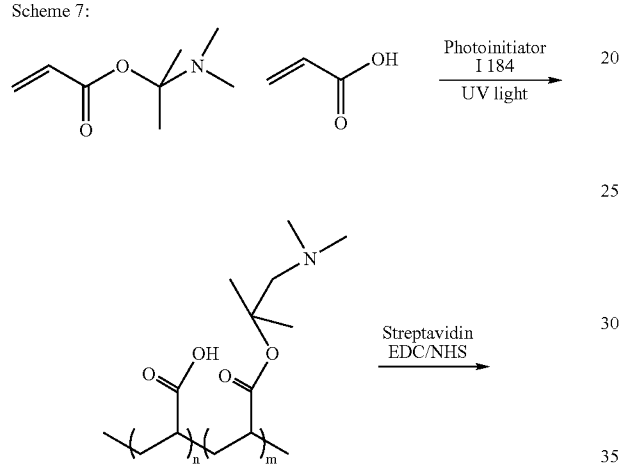

Scheme 8.

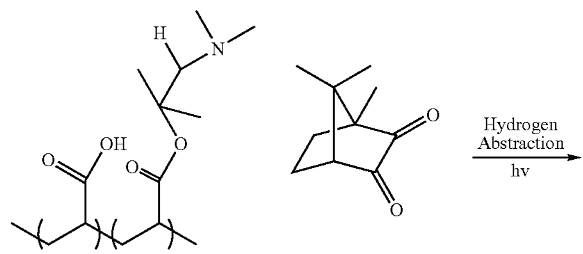

-continued

We claim:

1. A method for amplifying a molecular recognition interaction between a target and a probe comprising the steps of:

a. contacting the target with the probe under conditions effective to form a target-probe complex;

b. removing target not complexed with the probe;

c. contacting the target-probe complex with a photoinitiator label under conditions effective to attach the photoinitiator label to the target-probe complex;

d. removing photoinitiator label not attached to the target-probe complex;

e. contacting the photoinitiator-labeled target-probe complex with a polymer precursor solution;

f. exposing the photoinitiator-labeled target-probe complex and the polymer precursor solution to light, thereby forming a polymer; and g. detecting the polymer formed, thereby detecting an amplified target-probe interaction.

2. The method of claim 1, wherein the target comprises biotin, the photoinitiator label comprises avidin or streptavidin, and the photoinitiator label is attached to the target-probe complex by interaction between the biotin and the avidin or streptavidin.

3. The method of claim 1, wherein the target comprises single-stranded DNA (ssDNA) or RNA and the probe comprises ssDNA having a sequence complementary to at least a portion of the sequence of the target.

4. The method of claim 3, wherein the target comprises Influenza A, B, or C RNA.

5. The method of claim 1 wherein the target comprises one of an antibody or antigen and the probe comprises the other of an antibody or antigen.

6. The method of claim 1 wherein the target comprises a first protein, the probe comprises a second protein, and the first and second proteins are capable of molecular recognition.

7. The method of claim 1, wherein the photoinitiator is a radical initiator and polymer precursor solution is contacted with a gas to control the solution oxygen content during light exposure.

8. The method of claim 1, wherein the photoinitiator label comprises a radical initiator and the oxygen content of the polymer precursor solution is less than about $1\times10^{-5}$ moles/liter.

9. The method of claim 8, wherein the photoinitiator label comprises a macroinitiator.

10. The method of claim 1 wherein the photoinitiator label comprises a plurality of initiators.

11. The method of claim 10 wherein the photoinitiator label comprises a macroinitiator.

12. The method of claim 11, wherein the macroinitiator comprises a plurality of initiators attached to the backbone of a second polymer.

13. The method of claim 12, wherein the average number of initiators attached to the second polymer backbone is greater than about 100.

14. The method of claim 13, wherein the average number of initiators attached to the second polymer backbone is less than about 200.

15. The method of claim 11, wherein the time of light exposure is sufficiently long that the polymer forms in sufficient quantities to allow visual detection.

16. The method of claim 15, wherein the polymer forms a layer greater than about 1 micron thick.

17. The method of claim 16, wherein the polymer forms a layer greater than about 5 microns thick.

18. The method of claim 1, wherein the probe is attached to a solid substrate.

19. The method of claim 18, wherein nonspecific interactions between the substrate and the target are limited by prior application of a blocking agent to the substrate prior to step a) or by use of a crowding agent during step a).

20. The method of claim 18, wherein nonspecific interactions between the substrate and the photoinitiator label are limited by prior application of a blocking agent to the substrate prior to step c).

21. The method of claim 1, further comprising the step of removing unpolymerized polymer precursor prior to detecting polymer formation.

22. The method of claim 1 wherein during step e) the photoinitiator-labeled target-probe complex is contacted with the polymer precursor in the presence of a cross-linking agent and the polymer formed in step f) is a hydrogel.

23. The method of claim 22 further comprising the steps of i) contacting the hydrogel with a solution comprising a fluorophore, thereby allowing absorption of the fluorophore solution by the hydrogel and ii) removing excess fluorophore solution, both steps being performed prior to step g).

24. A method for identifying a target comprising the steps of providing a probe array comprising a plurality of different probes, wherein the probes are attached to a solid substrate at known locations; and amplifying the molecular recognition interaction between the target and the probes by the method of claim 1, wherein the target is contacted with the probe by contacting the probe array with the target and the location of the polymer formed indicates the probe which forms a target-probe complex with the target, thereby identifying the target.

25. The method of claim 24, wherein the probe array contains ssDNA, antigens, and proteins.

26. The method of claim 25, wherein the probe array contains ssDNA complementary to Influenza A, B, or C RNA, Influenza A, B, or C antigens, and proteins which capture proteins which form in the outside of Influenza A, B, or C viral particles.

* * * * *